United States Patent
Dunlavey et al.

(10) Patent No.: US 7,043,415 B1
(45) Date of Patent: May 9, 2006

(54) INTERACTIVE GRAPHICAL ENVIRONMENT FOR DRUG MODEL GENERATION

(75) Inventors: Michael Robert Dunlavey, Needham, MA (US); David J. Hermann, Chelsea, MI (US); Jeffrey Alan Wald, Cary, NC (US); Daniel Lee Weiner, Apex, NC (US)

(73) Assignee: Pharsight Corporation, Mountain View, CA (US)

( * ) Notice: Subject to any disclaimer, the term of this patent is extended or adjusted under 35 U.S.C. 154(b) by 907 days.

(21) Appl. No.: 09/823,214

(22) Filed: Mar. 30, 2001

Related U.S. Application Data

(60) Provisional application No. 60/265,750, filed on Jan. 31, 2001.

(51) Int. Cl.
*G06G 7/48* (2006.01)

(52) U.S. Cl. .............. 703/12; 703/2; 715/747; 715/763; 715/765; 702/19; 707/13

(58) Field of Classification Search ............. 703/12, 703/11, 2; 600/300; 707/104.1, 3; 345/848; 715/747, 763, 765; 702/19; 435/325
See application file for complete search history.

(56) References Cited

U.S. PATENT DOCUMENTS

| | | | | |
|---|---|---|---|---|
| 5,434,796 A | * | 7/1995 | Weininger | 703/12 |
| 5,860,917 A | * | 1/1999 | Comanor et al. | 600/300 |
| 5,962,317 A | * | 10/1999 | Hamzeh et al. | 435/325 |
| 6,051,029 A | | 4/2000 | Paterson et al. | |
| 6,069,629 A | | 5/2000 | Paterson et al. | |
| 6,078,738 A | | 6/2000 | Garza et al. | |
| 6,381,562 B1 | * | 4/2002 | Keane | 703/11 |
| 6,542,858 B1 | * | 4/2003 | Grass et al. | 703/2 |
| 6,647,358 B1 | * | 11/2003 | Grass et al. | 703/2 |
| 6,694,334 B1 | * | 2/2004 | DuLong et al. | 707/104.1 |
| 2002/0120431 A1 | * | 8/2002 | Keane | 703/11 |
| 2003/0156143 A1 | * | 8/2003 | Westenskow et al. | 345/848 |
| 2004/0093331 A1 | * | 5/2004 | Garner et al. | 707/3 |

OTHER PUBLICATIONS

Van Meurs et al., W.L. Pharmacokinetic-Pharmacodynamic Model for Educational Simulations, IEEE Transactions on Biomedical Engineering, vol. 45, No. 5, May 1998, pp. 582-590.*

(Continued)

*Primary Examiner*—Russell Frejd
(74) *Attorney, Agent, or Firm*—Townsend and Townsend and Crew LLP

(57) ABSTRACT

A method for interactively constructing pharmacological computational models is disclosed. A graphical user interface is presented through which a user may place and connect objects representing pharmacokinetic and pharmacodynamic elements. As the objects are placed and connected, they are converted into an internal format representing the statements of the corresponding computational model. These statements are actively presented to the user in a summarized form, as the computational model is constructed, to enable immediate verification of the model. This summarized form may be a surface syntax showing key equations that make up the model, or they may be graphs of behavior of one or more user-selected variables.

26 Claims, 12 Drawing Sheets

OTHER PUBLICATIONS

Kang et al., D. Bayesian Estimation in Pharmacokinetics/Pharmacodynamics Using Regenerative Sampling-Based Methods, Proceedings of the First Joint BMES/EMBS Conference Serving Humanity, Advancing Technology, Oct. 1999, p. 987.*

Jelliffe et al., R. Population Pharmacokinetic and Dynamic Models: Parametric (P) and Nonparametric (NP) Approaches, Proceedings 14th IEEE Symposium on Computer-Based Medical Systems, Jul. 2001, pp. 407-412.*

Katzper, M. Intrinsic Dynamics and Pharmacometric Model Discrimination, Proceedings of the 1995 Winter Simulation Conference, pp. 1066-1072.*

Michael R. Dunlavey, Performance Tuning: Slugging It Outl, Dr. Dobb's Journal, Nov. 1993.

Michael R. Dunlavey, Differential Evaluation: a Cache-based Technique for Incremental Update of Graphical Display of Structures, Software Practice and Experience, vol. 23, No. 8, Aug. 1993, pp 871-893 (Wiley).

High Performance System, Inc., http://www.hps-inc.com/index.html, Mar. 2001.

Gabrielsson et al., Pharmacokinetic and Pharmacodynamic Data Analysis: Concepts and Applications, 3rd edition, 2000, pp. 45-46, 175-176.

High Performance Systems, Inc. STELLA, An Introduction to Systems Thinking, 2001, 173 pages total.

* cited by examiner

| 402 | 404 |
|---|---|
| Const | a numeric constant |
| NamedConst | a numeric constant having a name, such as Male or Female |
| StrConst | a string constant such as 'this is a string' |
| Unit | a basic unit such as L(liters) or d(days) |
| GetPort | a reference to the value of a variable |
| Trinop | trinary operator, such as the conditional operator |
| Binop | binary operator, such as +, -, *, /, comparison, etc. |
| Unop | unary operator, such as unary minus, and logical .not. |
| TimesUnit | multiplication by a unit phrase |
| UnitBinop | binary unit operator, such as *, / |
| UnitPhrase | encapsulates a unit phrase |
| DelayFunc | the delay function. It's output equals its input delayed by an offset. |
| TableFunc | the tabular function. |
| Funcall | calls one of a set of built-in functions, such as sqrt, exp, ln, etc. |
| SetPort | stores a value into a variable |
| SetDerv | sets the derivative (rate of change) of a variable |
| DEvent | represents the action to be performed when an event fires. |
| CDistr | represents a univariate continuous distribution. |
| DDistr | represents a univariate categorical distribution. |
| DLogit | represents a categorical distribution determined by an input value, some offset values, and a link function. |
| Choose | represents block equivalent of the trinary conditional expression. |
| Subrcall | represents a call to an external user-written subroutine. |
| NewStmtSequence | represents a sequence of statements |
| StmtIfThenElse | represents an if-then-else statement |
| InitCF | initializes a closed form machine by setting its initial parameters. |
| Add1stOrdCF | modifies a closed form machine by convolving its parameters with a first order delay. |
| Add1stOrdInputCF | modifies a closed form machine by convolving its parameters with a first order delay. |
| CloneCF | copies one closed form machine into another. |
| GetValCF | reads the value of a closed form machine |
| AddDoseCF | adds a bolus dose to a closed form machine |
| AddRateCF | adds to the infusion rate in a closed form machine |
| IfLevel | a special if statement used to guard statements, causing them to only be executed at the proper distribution level, such as continuous, event, periodic, etc. |
| SetDiscrete | used to set a group of categorical variables that are jointly distributed. |
| DSwitch | used to choose among a set of continuous values on the basis of a set of discrete values. |
| MCorDistr | represents a multivariate continuous distribution with correlation matrix |
| MVarDistr | represents a multivariate continuous distribution with variance-covariance matrix. |
| MVarImport | represents a set of variables that are being imported. |

FIG. 4

```
1  if(iSubPop==0) then switch(SetDiscrete1(ddistr(2, 0.51, 0.49), Gender, 2),BodyWeight = no
2  A' = -(A*Ka)
3  Temp_00 = normal1(1,V_ETA_mean,V_ETA_sd,V_ETA_lo,V_ETA_hi)
4  V_ETA = V_ETA_mult*Temp_00
5  Volume = BodyWeight*1(L/kg)
6  Temp_01 = normal1(1,Pmax_ETA_mean+Pmax_ETA_sd, Pmax_ETA_lo, Pmax_ETA_hi)
7  Pmax_ETA = Pmax_ETA_mult*Temp_01
8  Placebo_Effect = 0.3
9  Temp_02 = uniform(1,Chance_lo,Chance_hi)
10 Chance = Chance_mult*Temp_02
11 Relief = 1
12 V = Volume
13 Pain_Relief_i = Relief
14 C = A1/V
15 A0' = C*CL
16 CP_i = C
17 Drug_Effect_C = C
18 A1' = A*Ka-C*CL
19 Drug_Effect = Drug_Effect_Emax*Drug_Effect_C**Drug_Effect_Hill/(Drug_Effect_EC50**Drug_Ef
```

FIG. 7B

INTERACTIVE GRAPHICAL ENVIRONMENT FOR DRUG MODEL GENERATION

RELATED APPLICATIONS

This application claims the benefit of U.S. Provisional Application Ser. No. 60/265,750, filed on Jan. 31, 2001.

BACKGROUND

1. Field of the Invention

This invention relates generally to computational models of dynamic processes within living organisms, and more particularly, to systems and methods for enabling generation of computational models of drug behavior.

2. Description of Related Art

Information regarding the behavior of drugs and diseases in the body of a living organism is needed for many purposes in biological science and industry. Generally, this information gives rise to two interrelated disciplines: pharmacokinetics, which is the study of the processes by which a drug is absorbed, distributed, metabolized and eliminated by the body, and pharmacodynamics, which is the study of the action or effects of drugs on living organisms.

Pharmacokinetics and pharmacodynamics are combined to study the efficacy of drugs and the progression of diseases, through the use of computational models. Such computational models are also commonly referred to as drug models or input/output models. Typically, these computational models are stored as software subroutines in a high level language, such as Fortran, for use in a variety of applications. Two applications in particular require these computational models: model fitting of clinical data, and simulation of clinical trials.

The traditional approach to generating these computational models is labor intensive and prone to extensive delays caused by human error. For example, in the case of generating a drug model, typically, a researcher will review all the information available concerning the way in which the drug behaves in the body of interest. In some cases, the researcher might also draw some rough sketches of compartments representing the various organs in the body and showing the flow of the drug through those organs. Then the researcher must figure out the differential equations that model that drug behavior, or alternatively, solve the differential equations using closed form solutions and determine the exponential equations. Finally, the equations must be translated into software, which in turn must be debugged.

Whenever software is written, human error and oversight invariably introduce bugs. Thus debugging of software is a necessary step, which can be tedious and time consuming. Further, the software debugging process is usually not complete until the researcher uses the software in an existing application and analyses the results to see if they make sense. These problems with drug model generation are exacerbated by the fact that many researchers are trained in the life sciences and are not necessarily experts at coding software. Using a trained computer programmer to work with the researcher may introduce needed coding expertise, but can also compound the problem by introducing a communication step to the process, which presents more opportunities for human error.

An early attempt to address the problem of researchers' lack of coding experience was the Advanced Continuous Simulation Language (ACSL). ACSL is a simulation language that allows a researcher to write differential equations, which are then converted into Fortran for insertion into a simulation program. While ACSL was an improvement, the language was not substantially different from the Fortran language itself, thus a researcher still needed knowledge of how Fortran programming works. Moreover, ACSL did not address any of the other significant problems, such as the difficulty of model verification before a simulation has been run.

Graphical drug model builders have also been created. For example, Pharsight Trial Designer 1.2, available from Pharsight Corporation, 800 West El Camino Real, Suite 200, Mountain View, Calif. 94040, includes a graphical model builder component, which allows a researcher to build a drug model using graphical blocks. Once the drug model is completed, the software generates code for use in trial simulation. The generated code implements the appropriate differential equations. However, when errors are made in the construction of the drug model, these errors may not be discovered until after a drug trial simulation is completed. Only after the results of the trial simulation are available is the researcher able to compare the products of the drug model with expectations. Since drug trial simulation frequently involves a large amount of processor time, this attempted solution is inefficient at accelerating the drug model creation process.

In addition to graphical model builders directed specifically to drug model generation, other graphical model builders have also been created. For example, Stella 6.0, available from High Performance Systems, Inc., 45 Lyme Road, Suite 300, Hanover, N.H. 03755-1221, is software designed to render and test mental models of everything from "how a bowl of soup cools to how a galaxy expands . . . and everything in between." While these types of software tools may be used to build drug models, their lack of focus on a particular problem set makes them less effective in the pharmacological context.

Moreover, when errors are made in the construction of a model, these errors are typically not found until after a simulation is completed. For simple simulations this is less of a concern, but for drug trial simulations, these errors can cause extensive delays in drug model verification.

SUMMARY OF THE INVENTION

One aspect of the invention is directed to a system and method for enabling graphical construction of pharmacological computational models using interactive equations display. A graphical user interface, which allows a user to place and connect objects that represent pharmacokinetic and pharmacodynamic elements, is presented. While the objects are placed and connected by a user, the objects are converted into an internal format, such as a parse tree, representing statements for the computational model under construction. Equations for the model under construction are derived from the statements, and actively displayed to the user.

This automatic expression of the graphical model in mathematical terms for examination by the user makes the graphical model builder interactive, thereby accelerating the model building and verification process.

Another aspect of the invention is directed to a system and method for enabling graphical construction of pharmacological computational models using interactive graphing of model outputs. A graphical user interface, which allows a user to place and connect objects that represent pharmacokinetic and pharmacodynamic elements, is presented. While the objects are placed and connected by a user, the objects are converted into an internal format, such as a parse tree, representing statements for the computational model under construction. These statements are then actively interpreted to generate a time-based simulation using the computational model, and one or more user-selected variables are plotted in a graph in real time, while the model is being constructed.

In one embodiment, the method further includes actively modifying the interpretation of the statements, either directly or by modifying the internal format, in response to user commands to modify variables and/or constants in the model under construction. The graph is thereby updated in light of the new variable information in real time. Additionally, in one embodiment, the plotting of the one or more user-selected variables retains a history of prior plots, thereby causing random variables in a model under construction to create fan like graphs, which visually demonstrates variability components in real time.

This real-time plotting of selected variables in a graphical model under construction allows a user to examine the outputs of a graphical drug model in an interactive fashion, thereby accelerating the model building and verification process.

Another aspect of the invention is directed to a computer system and computer readable medium for enabling graphical construction of pharmacological computational models using interactive equations display and interactive graphing of model outputs. Other and further aspects and features of the invention will become apparent from the following drawings and detailed description.

BRIEF DESCRIPTION OF THE FIGURES

Preferred embodiments are illustrated by way of example, and not by way of limitation, in the figures of the accompanying drawings, in which like reference numerals refer to like components, and in which:

FIG. 4 is a table showing primitives for an internal parse tree data structure for use in translating model blocks into equations according to one embodiment;

FIG. 7B is an illustration showing an exemplary drug model equations window for the drug model shown in FIG. 2A;

DETAILED DESCRIPTION OF THE INVENTION

The present invention is generally directed toward systems and methods employing a computer-presented graphical user interface through which a user can generate a drug model interactively. For ease in illustration, aspects and features of the invention are disclosed and described herein in terms of a single computer running locally stored software for designing drug models. However, after reading this description, it will be apparent to those skilled in the relevant art(s) that the invention may be implemented in alternative embodiments. For example, alternative embodiments include distributed systems in which a dumb terminal accesses the software over a network connection, and also editors that allow construction of alternative computational models, such as models of disease processes within the body and disease-drug interactions.

Figure 1:
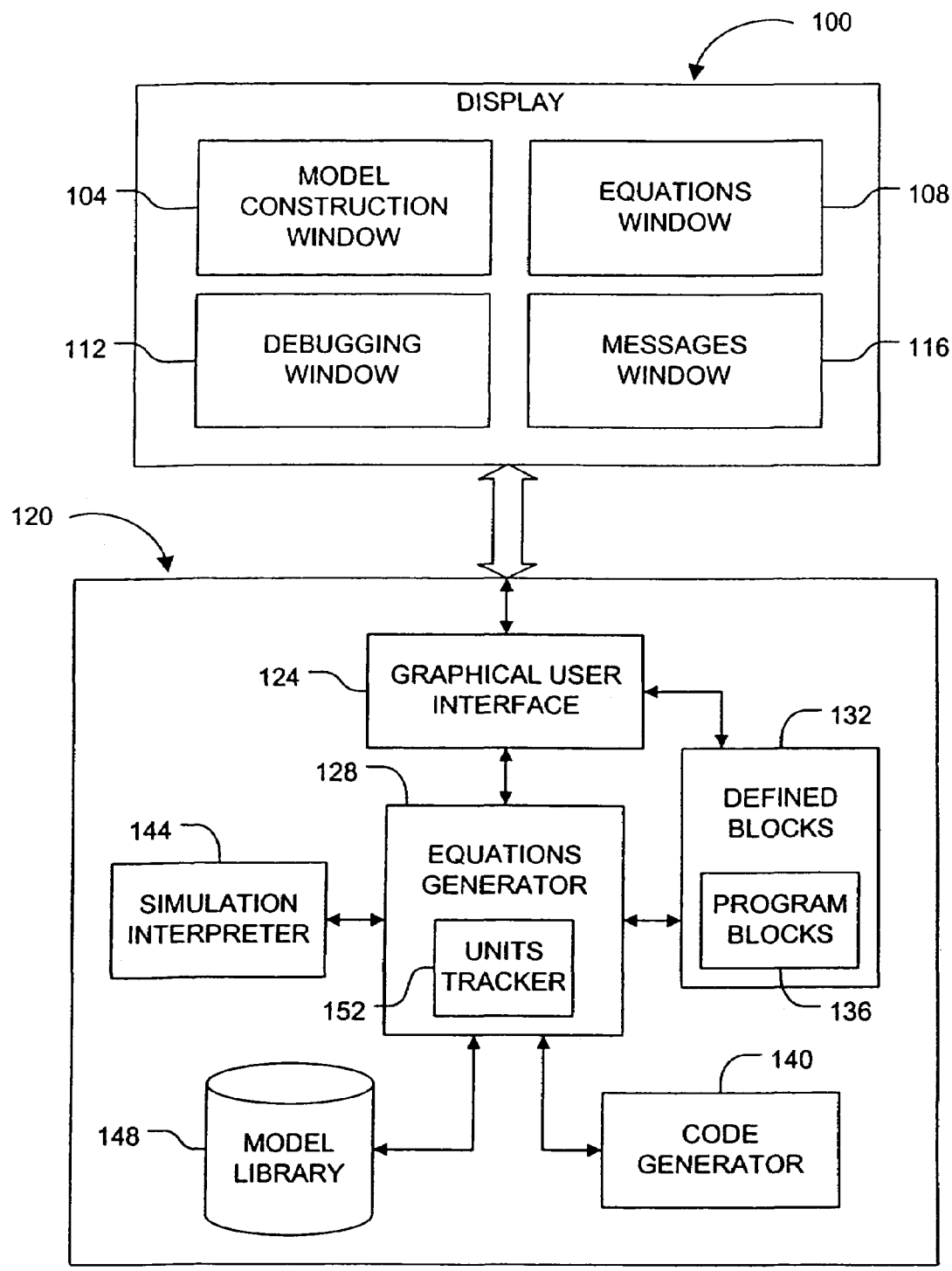
FIG. 1 is a block diagram illustrating components of a drug model editor according to one embodiment.

FIG. 1 is a block diagram illustrating components of a drug model editor according to one embodiment. The drug model editor includes a display 100 and a programmed computer 120. The programmed computer 120 includes a graphical user interface 124, an equations generator 128, a set of defined blocks 132, a code generator 140, a simulation interpreter 144, and a drug model library 148. In one embodiment, the set of defined blocks 132 includes one or more programmable blocks 136, and the equations generator 128 includes a units tracker 152.

The graphical user interface 124 presents various windows on the display 100, thereby enabling a user to construct, modify, view and debug computational models of drugs using graphic objects. In the illustrated embodiment, these various windows are divided into four general types: a model construction window 104, an equations window 108, a debugging window 112, and a messages window 116. While these windows are shown in FIG. 1 as non-overlapping, they may in fact overlap, be resized, etc., as would be apparent to those skilled in the relevant art(s).

The model construction window 104 displays the graphical model under construction. The equations window 108 displays equations derived from the graphical model. The debugging window 112 displays a plot of variables selected from the graphical model, either against time or against each other. Errors and warnings are listed in the messages window 116. Typical error messages include syntax errors, use of undefined variables in user code, misuse of units, divide by zero, etc.

The available functionality and presentation formatting for the windowing environment generated by the graphical user interface 124 is extensive and well appreciated by those skilled in the relevant art(s). In one embodiment, the graphical user interface 124 uses Microsoft Dialog Windows, which are part of the Windows' operating system. Alternative embodiments include any visual presentation wherein a drug model can be constructed using graphic objects, equations representing the drug model can be generated and displayed at the same time as the drug model is constructed, and the behavior of the constructed drug model can be tested and displayed at the same time as the drug model is constructed using real-time emulation.

In one embodiment, certain error messages, such as misuse of units, are always displayed within the model construction window 104 in a simplified messages window 116. Thus, the messages window 116 is not limited to a separate full window, such as a Microsoft Dialog Window, and in one embodiment is a simple box graphic placed on top of the drug model in the model construction window 104. This embodiment is discussed in greater detail below in connection with FIG. 3.

Figure 2A:
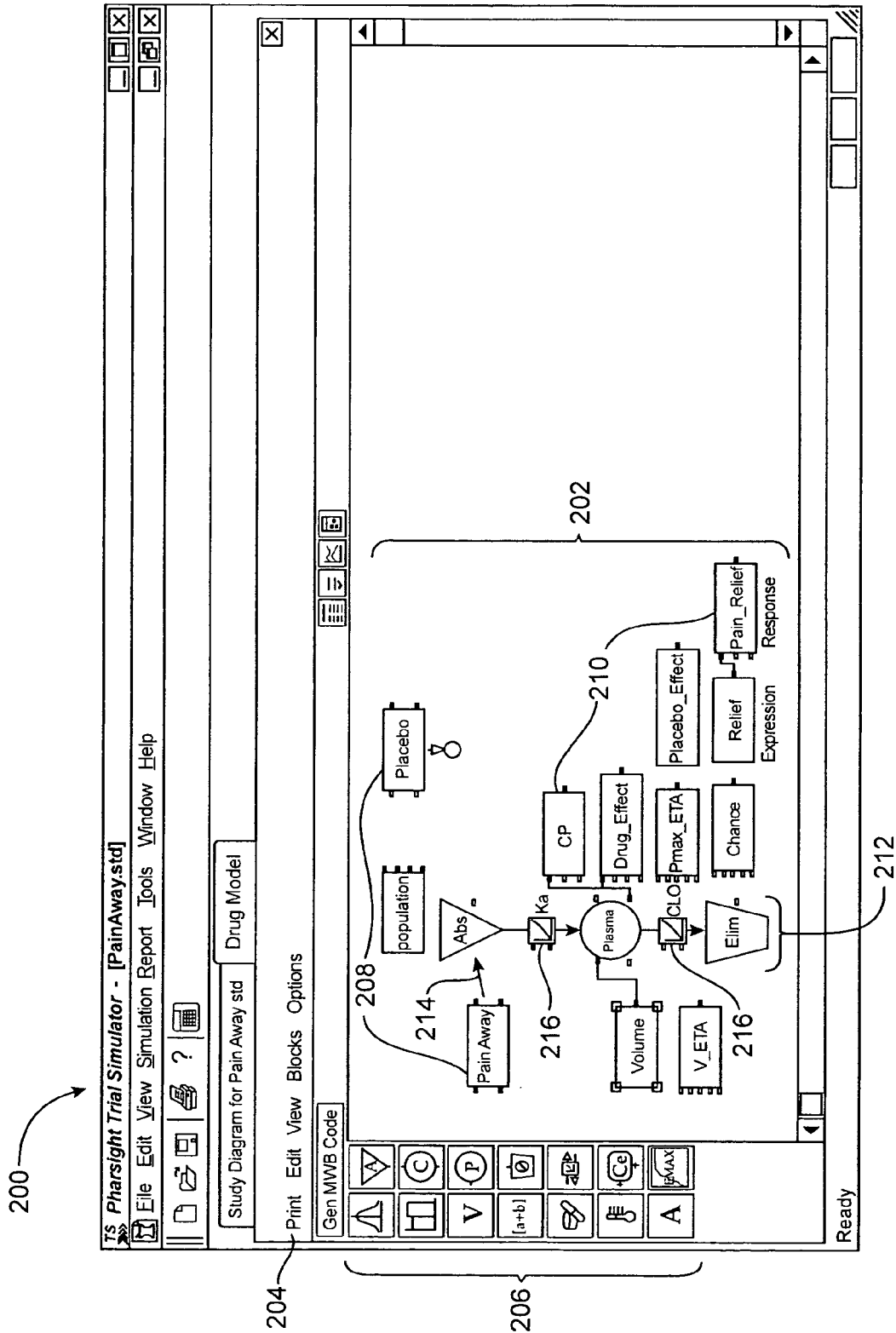
FIG. 2A is an illustration showing an exemplary drug model construction window according to one embodiment.

FIG. 2A is an illustration showing an exemplary drug model construction window according to one embodiment. Referring now to FIG. 2A, a drug model is constructed in a drug model construction window 200 by inserting blocks 202 selected from a menu 204 or by drag-and-drop from a set of icons 206. Each block has ports representing inputs and outputs that can be wired together. The ports correspond to variables in resulting equations.

In one embodiment, input ports are on the left of each block, and output ports are on the right. Any output port can be wired (by click and drag) to any input port. Additionally, a user can specify the names of the ports. In one embodiment, if an input port receives input from more than one wire, it receives the sum of the signals. The blocks 202 can be moved and/or resized by dragging. Groups of blocks 202 can be selected, either by lasso, or by control-click, and moved, cut, copied, or pasted.

In an alternative embodiment, connections between input and output ports are specified by the block placement, and no wiring of outputs to inputs is necessary to create a functioning drug model.

In one embodiment, the blocks are color coded by their function in the drug model. For example, formulation blocks 208 may be colored blue. A formulation block represents the intention to administer a particular drug (i.e. a path of drug administration). Thus, it is also referred to as a dosing/treatment block. Such blocks can be connected to compartment blocks, with the meaning that the drug will go into the connected compartment(s). A formulation block is a placeholder for information about subject adherence, such as delay time and 1-coin or 2-coin models. In one embodiment, placebos are also modeled as formulation blocks 208.

Response blocks 210 are colored green. A response block represents the intention to observe some variable of the drug model, such as concentration in the central compartment, pharmacodynamic effect, etc. Thus, it is also referred to as an observation block. These response blocks 210 may represent any number of protocol observables for use in a simulated clinical trial. For example, the response block CP in FIG. 2A represents a concentration in plasma observation for the drug PainAway.

Compartment blocks 212 represent any object that can store a given chemical compound. These objects are typically a specific organ or set of organs, but may also be manufactured objects such as a patch attached to the skin. Compartment blocks 212 are colored gray and are the heart of the pharmacokinetic model. Although the compartment blocks 212 are primarily intended to model pharmacokinetic compartments, they may also be used for modeling pharmacodynamic compartments. Generally, there are four types of compartments: absorption, central, peripheral, and elimination. Central and peripheral compartments, such as plasma and liver, can optionally have a volume parameter and are therefore able to represent relationships between amount and concentration of particular compounds.

Elimination compartments are typically not shown, but a graphic for elimination compartments is included in this example embodiment for the purpose of clarity.

Absorption compartments are used to represent a reservoir from which a drug is absorbed into the body, such as the gut. For example, a drug input arrow 214 represents oral presentation of formulation PainAway, in which the medication is entered into the gut. From there it is absorbed via the absorption flow into the plasma compartment. This pathway can be used both for bolus (i.e. a pill) or infusion (i.e. an administration of an amount of drug that takes an extended length of time), or any combination thereof. For example, a patch is a treatment regimen that is both an initial bolus and a slow release, thus it could be modeled using the single absorption compartment, formulation, and arrow. Alternatively, it could be modeled using multiple formulation blocks and/or multiple absorption compartments.

Between compartment blocks 212 are flow blocks 216. The flow blocks 216 are used to connect compartment blocks to represent the flow of chemical compound moving from one compartment to another at a certain rate. Flow blocks 216 can be unidirectional or bi-directional. They can also model reactions in which one chemical compound is transformed into another, such as a metabolite. The rate at which material flows from one compartment to the other can be specified in multiple ways, including any of the following: (1) a simple rate parameter, or micro parameter; (2) a clearance parameter; (3) Michaelis-Menten (saturating) kinetic parameters; or (4) a user-code expression. Any flow can be specified to be bi-directional if it is parameterized by a simple rate parameter. Additionally, any flow can have a bioavailability factor specified.

Of most interest in pharmacokinetics are the rates of flow between compartments as a function of time. This is discussed in greater detail below in connection with FIG. 5B.

In addition to the blocks discussed above, additional blocks 202 are provided. These additional blocks can be thought of as falling into four general categories, although these categories are not definitive and tend to overlap one another: (1) basic blocks, (2) math blocks, (3) pharmacodynamic blocks, and (4) other blocks.

In addition to the blocks discussed above, the basic blocks include a population block, an effect compartment block, a formulation block, an annotation block, and a group block. The population block allows specification of variables that define the individual properties of each subject, such as age, gender, body weight, renal clearance, etc. These population variables are also known as population covariates, subject covariates, or just covariates. The population block also allows statistical distributions to be associated with these covariates: either univariate or multivariate distributions. Distributions are categorical or continuous. All continuous distributions have optional high and low truncation limits, and any set of variables can be joined into a joint multivariate distribution.

The shape of each univariate distribution is chosen from among: categorical, normal, lognormal, poisson, weibull, beta, beta with mean and standard deviation, uniform, constant, binomial, negative binomial, exponential, logistic, chi-square, student's t, gamma, and inverse gamma distributions.

Each multivariate distribution can contain either or both of categorical or continuous variables. In the case that a multivariate distribution contains more than one continuous variable, the shape of the distribution is chosen from among normal, log-normal, and student's t, with either a correlation matrix or a variance-covariance matrix.

The population block also allows several sub-populations to be modeled in such a way that the parameters of each univariate or multivariate distribution can differ among different sub-populations. Additionally, within any given sub-population, the distribution may be determined by importing from a file of data, as specified by the user.

An effect compartment block represents a pure concentration in tissue, where the rate parameter of build-up is the same as the rate parameter of loss: $dY/dt=(X-Y)*K$. An effect compartment is also known as a "biophase."

As is known in the relevant art(s), for a typical drug to have an effect in the body, that drug must get to the location where the effect will occur. Typically, that means the drug must get into a particular kind of tissue, next to a particular kind of cell and bind with one or more specific receptors. The effect compartments are used to model the drug getting from the blood to where it actually does its work, i.e., to model the concentration of the drug next to the cells of interest).

Of significant concern is the amount of the drug next to the cells of interest. For this reason, the volume of an effect compartment is generally irrelevant. In its most general form, an effect compartment represents a delay between the time the drug gets into the blood and the time it begins to cause effects. The effect compartments are purely mathematical compartments, to which a response block may be attached.

An annotation block allows a block of text to be displayed in the graphical drug model, in a variety of fonts, colors, and sizes. A group block serves to enclose a set of other blocks. The blocks inside the group can be optionally visible or hidden, and the entire group can be moved and/or resized as a unit.

The math blocks include a continuous distribution block, a categorical distribution block, a multivariate distribution block, a choose block, an adder block, a multiplier block, a table block, an exponentiate block, a log block, a square block, a squareroot block, an inverse block, an integ block, and a delay block. The choose, adder, multiplier, table, exponentiate, log, square, squareroot, inverse, and integ blocks correspond simply to their respective mathematical functions.

The choose block implements a multiplexer. The adder block adds together two or more input signals. Each input can optionally be negated, so as to be subtracted from the sum, rather than added. The multiplier block multiplies together two or more input signals. Each input can optionally be inverted, so as to divide into the result, rather than multiply. The table block allows an arbitrary function to be entered in tabular form. The output is determined from the input by table lookup with interpolation. The table block can have multiple columns so as to have multiple output variables. The output of the exponentiate block is the exp function applied to the input. The log block output is the natural logarithm of the input. The square block output is the square of the input. The squareroot block output is the square root of the input. The inverse block output is 1 divided by the input. The integ block output is the time integral of the input (i.e. $Y=dX/dt$, where X is the input).

A continuous distribution block represents a quantity that is known to be variable over time, and for which there is no limit to the number of different values it can take on. When the drug model is used for trial simulation, the available kinds of distributions are normal, lognormal, poisson, weibull, beta, beta with mean and standard distribution, uniform, constant, binomial, negative binomial, exponential, logistic, chi-square, student's t, gamma, and inverse gamma. When the drug model is used for model fitting, the available kinds of distributions are normal, lognormal, and constant.

When the drug model is used for trial simulation, the distribution allows the user to specify an evaluation frequency level, which is evaluated either continuously, whenever an event such as administering a dose or taking an observation occurs, periodically, once per subject, once per center, or once per trial.

A categorical distribution block represents a quantity that is known to be variable over time, and for which the number of possible different values is finite and small. The categorical distribution allows the same evaluation frequency levels as the continuous distribution.

A multivariate distribution block represents multiple quantities that are known to be variable over time. The evaluation frequency can be specified as above. The variable can be specified to be singly or jointly distributed in the same way as they can in the population block except that there are no sub-populations. It can be specified that the distribution should be generated by import from a file, as in the population block.

In the delay block, the output is equal to the input delayed by a time offset. Unlike an effect compartment block, which can also be used to introduce delay, the delay block does not utilize a differential equation. Thus, the delay block may be preferable in certain drug models, such as a pill that does not begin being absorbed until five minutes after ingestion.

The pharmacodynamic blocks include a linear block, an emax block, an indirect block, a discrete effect block, and an event block. In the linear block, the output is a linear function of the input. Thus, output $Y=X*A+B$ where X, A, and B are inputs. In the emax block, the output $Y=EMAX*C\hat{}Hill/(C\hat{}Hill+EC50\hat{}Hill)$, where C, EMAX, EC50, and Hill are inputs.

The emax block represents the most common model of how concentration causes an effect. As discussed previously, drugs bind to receptors on cells in order to cause effects. This binding of receptors is a chemical reaction, thus there is a rate at which the chemical binds and another rate at which the chemical unbinds, for each level of concentration. But because there is always an unbinding rate, the receptors will never be 100% bound by the drug, no matter what the level of concentration. Thus the effect of the drug approaches an asymptotic limit, the Emax, as the drug concentration next to the receptor sites increases.

The amount of concentration needed to obtain half the effect of this limit is called the EC50 of the drug: the effect concentration at 50% of the Emax. The EC50 is essentially an inverse measure of how effective the drug is, and is a commonly used method of specifying a drug's effectiveness. A user can specify the EC50 of the drug by using the emax block, and then wire the output of the emax block into a response block to connect the drug's effectiveness with an observable quantity. Note that the emax block represents a simple computation, so there is no differential equation associated with it.

The indirect block is somewhat like a combination of an emax block and an effect compartment block. Its input governed by an emax factor, and its output is a function of the amount in the block. Thus, the indirect block employs a differential equation.

The indirect block is commonly used to model the situation where the body generates a substance and the generation and elimination of that substance is controlled by a drug. This is common, for example, for neuroactive drugs. The indirect block implements one of four indirect response models. (1) stimulation of buildup ($dY/dt=F*Kin-Y*Kout$), (2) inhibition of buildup ($dY/dt=(1-F)*Kin-Y*Kout$), (3) stimulation of loss ($dY/dt\ Kin-Y*F*Kout$), and (4) inhibition of loss ($dY/dt=Kin-Y*(1-F)*Kout$). For each of the equations above, $F=X/(X+EC50)$, and X, EC50, Kin, and Kout are inputs.

The discrete effect block is used to model a categorical response, such as a patient's answers to a questionnaire. Because different people who are in the same state chemically will give different answers, the discrete effect block should include a random element, which is preferably definable. Thus, $P(Y>i)=L(X+A(i))$, where Y can take one of n output values, 0 through n-1, and L is the inverse of a link function. Based upon the strength of the input, the probability of each particular output is increased or decreased in a manner defined by the link function. The inverse link functions L(x) include logit, probit, log log, complementary log log, linear, and signum (impulse). They are defined as follows:

| | |
|---|---|
| logit: | $L(x) = exp(x)/(1 + exp(x))$ |
| probit: | $L(x) = NCD(x)$, where NCD is the gaussian normal cumulative distribution function |
| log log: | $L(x) = exp(-exp(-x))$ |
| complementary log log: | $L(x) = 1 - exp(-exp(x))$ |
| linear: | $L(x) =$ if $x < 0$ then 0, else if $x > 1$ then 1, else x |
| signum: | $L(x) =$ if $x < 0$ then 0, else 1 |

All of these functions monotonically increase from zero at minus infinity to one at plus infinity. Note that the signum function is a way of saying there is no randomness at all; the function is a simple threshold.

The event block simulates events that take place at unpredictable times, such as seizures. The block has a sampling interval, which is a length of time that it waits between sampling. When it samples, it determines if an event occurred during the prior sampling interval, or how many events occurred during the interval. User-code statements are added to the event block to specify actions to be taken upon each occurrence.

The block can be used in two ways, probability or hazard. When it is used in probability mode, it has a probability expression P. When it samples, it reports one occurrence with probability P, otherwise no occurrence. When it is used in hazard mode, it has a hazard expression H. When it samples, it determines the number of occurrences by evaluating a Poisson distribution. The mean of the Poisson distribution is the time integral of the H expression over the interval.

The other blocks include an expression block, an action-at-times block, a model variables block, and a procedure block. The expression block allows the user to specify the block's output to be a user-programmed expression of its input(s). The action-at-times block allows the user to specify actions to be performed at specific times in the simulation. User code statements specify the actions. The times are specified by user code expressions, and may also be random. This allows models to contain parameters that relate to the time of an event, such as time of urination, or time of entero-hepatic reflux. The model variables block allows the user to specify named variables that can be used either as model parameters, or as history-keeping variables, such as counters or disease-state.

The procedure block allows the user to specify differential equations, and functional variables. A differential equation consists of a named variable (also known as an integrator variable), an initial value expression for the integrator variable, and a rate expression for the integrator variable. A functional variable consists of a named variable (also known as a procedure variable), an initial value expression, and optional statements to set its value. The functional variable cannot be used to hold history. It is only a function of other variables constituting the state of the simulation, such as model variables and integrator variables.

As each variable is added to a procedure block, the variable becomes an output of the block. The only variables that may be set in a procedure block are the local procedure and integrator variables, although global variables can be referenced, and the local procedure variables are all non-static. These limitations are placed on the procedure block to avoid the problems that could otherwise be created by the user. For example, if a user were to change a global variable inside a procedure block, there may be too much opportunity for human error to introduce bugs into the trial simulation, possibly reducing the benefits of the invention.

In addition, a user is prevented from placing a differential equation within conditional code. If a user were to specify, inside a procedure block, a differential equation that is dependent on an if statement, this could make the drug model inaccurate. During a trial simulation, the value of each differential equation must be calculated at each time step for the simulation to work properly, and thus the calculation of a differential equation cannot be left up to the state of the program at run-time.

Referring again to FIG. 1, as each defined block 132 is added to and connected with the graphical drug model using the graphical user interface 124, the equations generator 128 creates the equations that correspond to the selected blocks and connections. In one embodiment, the equations generator 128 creates internal format statements, which are then displayed in a visible surface syntax in the equations window 108. This will be discussed in greater detail below. As discussed above, a number of the defined blocks 132 comprise user-programmable blocks 136. In order to implement these user-programmable blocks 136, a simple programming language is provided.

The programming language comprises a syntax of expressions and statements. Expressions represent values to be computed, and statements represent actions to be performed. Although a particular embodiment is described herein, those skilled in the relevant art(s) understand that multiple variations on the basic programming language are equally applicable.

In one embodiment, the statements include the following: (1) sequence=perform a sequence of statements, (2) if-then-else=perform statements conditionally, (3) call=call a Fortran subroutine, (4) assignment=compute a value and store it in a variable, and (5) differential equation=specify the rate of change of a variable.

In one embodiment, expression operators include the following: (1) expression grouping using "(..)", (2) unit specification using "{..}", (3) prefix operators including "−", ".not.", and "!" (having their standard meanings), (4) infix arithmetic operators including "**", "*", "/", "+" and "−" (having their standard meanings), (5) infix comparison operators including ".ge.", ".le." ".ne." ".eq." ".gt.", and ".lt.", and also ">="" "<=", "!=""<>", "==", ">", and "<" (having their standard meanings), (6) infix logical operators including ".and.", "&&", ".or.", and "II" (having their standard meanings), and (7) the conditional operator "x ? y: z" (where if x is true, return y, and otherwise return z).

In one embodiment, standard functions are provided, including the following: (1) "sqrt" for square root, (2) "ln"

for natural log, (3) "exp" for exponentiation, (4) "sin" for sine, (5) "cos" for cosine, (6) "atan2" for arctangent (fullcircle), (7) "floor" for greatest integer less than or equal to x, and (8) "abs" for absolute value. Random functions are also provided, including: (1) "unif" to compute a uniformly distributed random number, (2) "normal" to compute a normally distributed random number, and (3) "lognormal" to compute a lognormally distributed random number.

The provided functions may be used with any of the variable types, including: input ports, output ports, procedure variables, integrator variables, model variables, T, and bDropped. T is a variable representing time, and bDropped is a boolean variable indicating if a subject has been dropped out of a study. Additionally, various constants may be specified in various variable types, as is well understood in the relevant art(s), e.g., numeric constants such as 3, 3.1415926, 3e4, 3d4, 3d–4, 0.001d60, string constants such as 'this is a string', and named constants such as Male or Female. Notably, in one embodiment, string constants are only allowed to appear as arguments to subroutines.

Figure 2B:
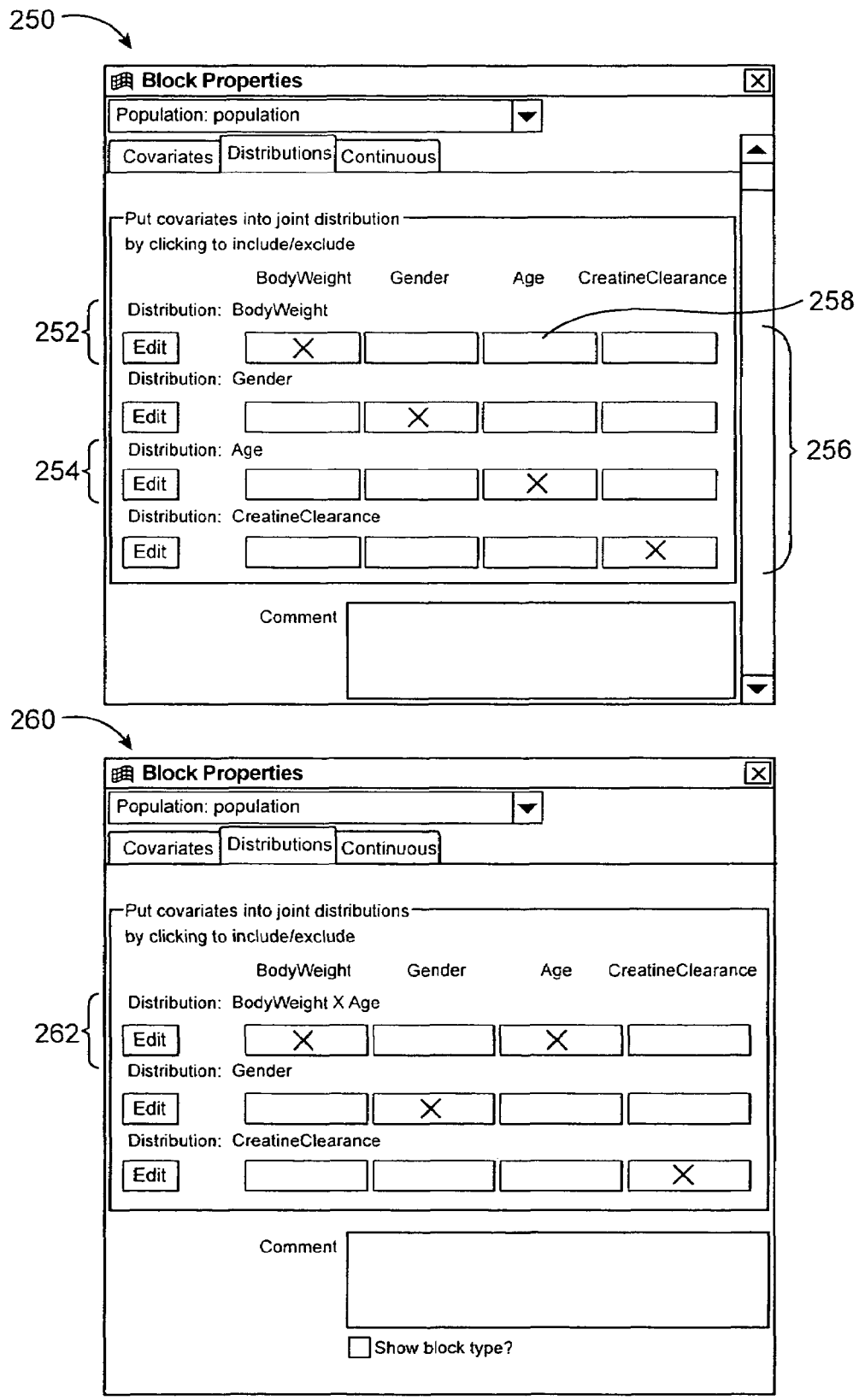
FIG. 2B is an illustration showing a dynamic graphical interface methodology as used in defining joint multivariate distributions according to one embodiment.

FIG. 2B is an illustration showing a dynamic graphical user interface methodology as used in defining joint multivariate distributions according to one embodiment. A block properties window 250 is opened for a population block by a user, such as by double clicking on population block in a graphical drug model. The block properties window 250 shows the various population variables, including Body-Weight in a BodyWeight distribution section 252 and Age in an Age distribution section 254. The block properties window 250 also shows the interrelationships of the population variables, and allows editing of the distributions by clicking the edit buttons.

The interrelationships of the population variables are shown by the X's, or lack thereof, in the interrelation buttons 256. To interrelate BodyWeight and Age, all the user need do is click the interrelation button 258. This causes the Body-Weight and Age variable to become interrelated, and the block properties window 250 becomes the block properties window 260. In the block properties window 260, Body-Weight and Age are now shown to be interrelated in a BodyWeightXAge distribution section 262, and their joint multivariate distribution can be edited by clicking the appropriate edit button.

FIG. 2B demonstrates the principle of a dynamic graphical user interface, which is preferably used in all of the graphical user interfaces (GUIs). Everything about each GUI is variable. When the window size is increased, more options and/or buttons appear. When one button is clicked, more and/or less buttons may be presented. This dynamic interface is implemented using the principles of Differential Execution/Evaluation. For background information regarding Differential Execution/Evaluation, see the Appendix, which is a copy of the article entitled Differential Evaluation: a Cache-based Technique for Incremental Update of Graphical Displays of Structures, written by Michael R. Dunlavey, and published in Software—Practice and Experience, Vol. 23(8), pp. 871–893 (August 1993).

Differential Execution is used to implement the dynamic interfaces, or "dialogs", described above. As is known in the relevant art(s), a dialog box is a window that contains a number of "controls", which are child windows designed to solicit information from the user. Examples of controls are "edit controls", in which the user can enter textual information, "button controls" which look and act like labeled push buttons, and "static controls" which simply display some text for the user to read.

The usual method by which a programmer specifies the design of a dialog box is to create a textual description of the dialog box and its controls within a text file (typically called a "resource" file). An example of such a description is the following:

```
IDD1_NEW_STUDY DIALOG DISCARDABLE 0, 0, 251, 199
STYLE DS_MODALFRAME | WS_POPUP | WS_VISIBLE | WS_CAPTION |
WS_SYSMENU
CAPTION "New Study"
FONT 8, "MS Sans Serif"
BEGIN
    LTEXT           "Available designs",IDC_STATIC,7,6,56,8
    LISTBOX         IDC1_LB_DESIGNS,7,16,124,90,
                    LBS_NOINTEGRALHEIGHT | WS_VSCROLL |
                    WS_TABSTOP
    GROUPBOX        "Study Parameters",IDC_STATIC,135,13,
                    109,94
    LTEXT           "Treatment Arms:",IDC_1ST_TREATS,141,28,
                    54,8
    EDITTEXT        IDC1_EB_TREAT,195,26,28,14,
                    ES_AUTOHSCROLL
    LTEXT           "Periods:",IDC1_ST_PER,141,49,26,8
    EDITTEXT        IDC1_EB_PER,171,46,33,14,ES_AUTOHSCROLL
    CONTROL         "Study has Lead-in phase",
                    IDC1_CB_LEADIN,"Button",BS_AUTOCHECKBOX
                    | WS_TABSTOP,141,68,94,10
    GROUPBOX        "Design Description",IDC_STATIC,7,110,
                    237,46
    LTEXT           "Static",IDC1_ST_DESC,15,121,222,32
    CONTROL         "Use &Wizard to guide in defining basic
                    study",IDC1_CB_WIZARD,"Button",
                    BS_AUTOCHECKBOX | WS_TABSTOP,7,162,176,
                    10
    DEFPUSHBUTTON   "OK",IDOK,7,179,50,14
    PUSHBUTTON      "Cancel",IDCANCEL,100,179,50,14
    PUSHBUTTON      "Help",ID_HELP,194,179,50,14
END
```

In general, the above description defines a dialog box called "New Study", specifies its size, and gives a list of its controls. LTEXT specifies a static control at a certain position and size relative to the dialog box, containing a left-justified string of text. EDITTEXT specifies an edit control at a certain position and size, in which the user can enter and/or edit a character string. PUSHBUTTON specifies a button control at a certain position and size, with a textual label, that the user can click in order to cause an action. Each control generally contains a string of 4 numbers, giving its offset relative to the upper left corner of the dialog box, and its width and height. It also typically contains a symbolic identifier, such as IDC1_LB_DESIGNS, ID_HELP, IDC_1ST_TREATS, that the remainder of the application can use to manipulate the controls of the dialog when it is used at run time. Controls also can contain additional "style markers" giving additional information about the appearance and behavior of the controls, such as ES_AUTOHSCROLL which means that the edit control having that style automatically scrolls horizontally as the user moves the cursor within the control.

Dialogs specified in this way are static in the sense that the size, position, contents, and visibility of the controls and of the entire dialog box are essentially fixed, and can only be altered at run time with a certain level of effort and skill on the part of the programmer. Dynamic dialogs, by contrast, allow nearly all aspects of the dialog and its controls to be variable in real time, with little or no effort on the part of the programmer. This allows a single dialog box to serve a much wider variety of needs.

The following example uses the C++ programming language to create dynamic dialogs, but any suitable programming language may be used. To specify a dynamic dialog, one writes a class for it, derived from the CDynDialog base class, and having a function called Contents( );

class CMyParticularDialog: public CDynDialog {public:
    void Contents( );
};

The Contents ( ) function is then written to specify the contents of the dialog. For example:

```
void CMyParticularDialog :: Contents(){
    // give title, position, and size of dialog
    Dialog("My Title", 100, 100, 300, 200);
    // a static control
    Static(10, 10, 30, 9, SS_LEFT, "some text");
    // an edit control
    Edit(10, 20, 30, 40, ES_MULTILINE, &sMyString);
    // a pushbutton control
    if (PushButton(10, 30, 30, 9, "Do Something")){
        // write code in here to take some action that
        // will be performed when the button is pushed
        DD_THROW;
    }
}
```

Thus, the Contents ( ) function is serving the same function as the resource script above, except that it is in the C++ language. The primary advantages of this approach are (1) everything in the dialog can be calculated at the time the dialog is created, such as size and textual content, (2) it is much more tightly integrated with the application data and it is not necessary to write code to move information in and out of the edit controls, and (3) it is not necessary for the controls to have symbolic identifiers, because the action code for the controls can be specified adjacent to the controls themselves.

In addition, the contents and attributes of the controls can be made to be variable, not just at the time of dialog creation, but in real time, with the proper programming of the underlying class. This is done by means of the technique called Differential Execution or Differential Evaluation. In this technique, any given procedure, such as the Contents ( ) function given above, can be executed repeatedly (typically 5 times/sec) in such a way that the subroutines that it calls can determine how their arguments may have changed since the prior execution and can effect incremental changes in what they are displaying. For example, the Static function specifies a static control to display a text string at a given position and size. On any execution, if the text string differs from what it was on the prior execution, the static function can update the text string on the screen. If the size or position changes, then the Static function can move the text string on the screen. The same reasoning applies to all controls and to the dialog box itself The phrase that the subroutines "maintain" their visible manifestations on the screen is used because they not only cause them to appear when the dialog is first displayed, but they see to it that the displayed data remains correct in real time, and can even cause the visible manifestation to be erased from the screen.

In addition to having subroutines that are aware of their prior arguments, it is possible to have normal structured programming contructs in the Contents ( ) routine as well, provided that they are also implemented so as to be sensitive to prior arguments. In one embodiment, these structured programming constructs are implemented by means of macros starting with the letters "DD". Some of the macros include: DDIF, DDEND, DDELSE, DDELIF, DDFOR, and DDSWITCH. One example of the code is:

DDIF(x>3)
    Static(10, 10, 40, 9, SS_LEFT, "Some Text");
DDEND

DDIF causes the static control "Some Text" to appear or disappear in real time depending on the current value of the expression "x>3". Another example is:

DDFOR(i=0, i<n, i++)
    Edit(10, 10+i*9, 40, 9, &sa[i]);
DDEND

DDFOR causes an array of n edit fields to be displayed, allowing the user to edit the contents of an array of string variables "sa". If the value of n changes, in real time, the number of visible edit controls also changes in real time.

The Contents( ) function can also be broken up into subroutines, so that the dialog specification can be modularized into pieces that can be used for different purposes. This, together with the DDSWITCH construct, enables the same screen area of the dialog to be used with very different sets of controls depending on the type of object being presented in the dialog.

The core of the CDynDialog class is its history-keeping mechanism. For this purpose, it keeps a first-in-first-out (FIFO) of binary data. This FIFO functions as a sequential file in which the arguments of each control subroutine are written, in order as the subroutines are executed. As each subroutine executes, for example, the Static subroutine, it writes its current arguments onto the front end of the FIFO. Then it reads from the back end of the FIFO, into a shadow set of argument variables, the values that the arguments had on the prior execution. Then it compares the values of the current arguments against the values of the prior arguments. If the arguments have not changed, it makes no change to the visible manifestation of the actual control window. If the string content of the control has changed, or if the position or size has changed, it modifies the control window accordingly. In order to do this, it must remember the window handle of the actual control window, and it does this by recording that in the FIFO as well.

As will be understood by those skilled in the relevant art(s), something different has to happen at the beginning of this process. The class contains an integer variable called the "mode" having values denoted DD_SHOW, DD_UPDATE, DD_ERASE, and DD_COMMAND. The behavior of the control subroutines is conditional on the value of the mode. In the normal repetitive execution discussed above, the mode is DD_UPDATE. On the very first execution, for example when the dialog is first being displayed, the mode is DD_SHOW. In this mode, the subroutines know that there is no prior history, so they write their arguments at the front end of the FIFO, but they do not read prior values from the back end of the FIFO because there aren't any. Instead, they actually create and display the actual control window that they will maintain on subsequent executions.

The mode denoted DD_ERASE is the mirror image of DD_SHOW. When the dialog is being closed, the Contents ( ) function is executed one last time in DD_ERASE mode. In this mode, the subroutines completely ignore the current values of their arguments and do not write them onto the front end of the FIFO. However, they do read the prior values of their arguments from the back end of the FIFO, including the handle of the actual control window, and use this information to destroy the actual control window.

It will be understood by those skilled in the relevant art(s) that it is not necessary to perform a DD_ERASE execution before closing the dialog. The dialog window may be destroyed directly, which will cause the actual control windows to be destroyed along with it. This approach is less desirable, however, because the DD_ERASE can be used for other purposes as well. For example, when the DDIF construct is used, as described above, the real-time appearance and disappearance of the Static control may be effected by using the DD_SHOW and DD_ERASE modes in a local transient fashion within the scope of the DDIF statement. In order to do this, the DD IF statement itself is sensitive to the current and prior value of its test expression, and it can locally change the mode. In one embodiment, all of the structured programming constructs make use of the mode variable to cause controls or sets of controls to appear or disappear in real time.

The remaining mode, DD_COMMAND, is used to signify that some user-interface event has taken place. For example, if the user clicks a button, the operating system sends a command message to the dialog box control program embedded within the class. This program records the identifier of the control that was clicked and then runs the Contents ( ) function in mode DD_COMMAND. In this mode, the control subroutines read their old arguments (non-destructively) from the FIFO. From this, they can retrieve the handle of their actual control windows. Each subroutine decides if the current command is relevant to its window, and if so, takes appropriate action. In the case of clicking a button, the PushButton control subroutine returns the boolean value TRUE, causing the button action code to be executed. This is typically followed by throwing control back out of the Contents ( ) routine after the action has been performed.

Figure 3:
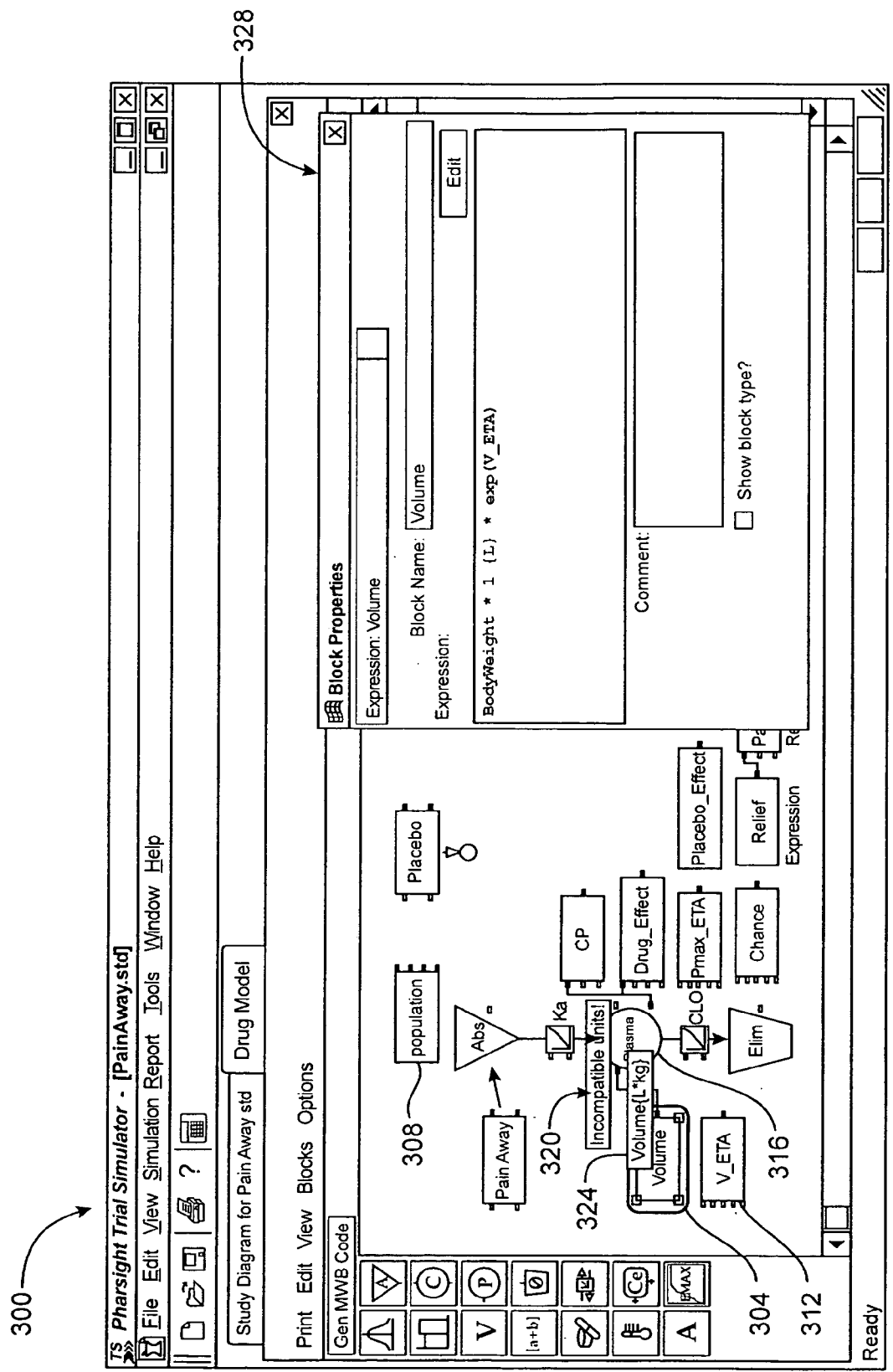
FIG. 3 is an illustration showing an exemplary incompatible units notification according to one embodiment.

FIG. 3 is an illustration showing an exemplary incompatible units notification according to one embodiment. In one embodiment, all variables have associated units data, thus each defined block 132 has units data associated with its input and output ports. Some of the defined blocks 132 represent common drug model components and have default units data associated with their ports. For example, a central compartment block is usually used to model blood plasma, thus it typically has a volume associated with it. Thus, in one embodiment, the upper left port on a central or peripheral compartment is a volume port, which has default units data of liters (expressed as "{L}"). The remaining defined blocks 132 have default units data specifying that the units are dimensionless (unitless).

The equations generator 128 includes a units tracker 152, which checks for incompatible units whenever an equation is created. In one embodiment, the error tracker 152 is integrated into the equations generator 128. Thus, the physical dimensions of variables are treated as data types and are combined and tracked as part of the compilation parsing of the defined blocks 132, which generates the equations. This automatic capture of unit measurement errors in the expressions defined by selected blocks is a significant advantage in drug modeling. In pharmacological studies, the physical meaningfulness of the model is often critical.

Referring to FIG. 3, a model construction window 300 shows a drug model under construction by a user. The user has created an expression block 304, labeled "Volume", and defined its output to be BodyWeight*1 {L}*exp(V_ETA). "BodyWeight" is a covariate defined by the population block 308, and it has units of {kg}. "1" is a constant with defined units of {L} specified by the user. "Exp(V_ETA)" is e to the power of "V_ETA", which is a model variable defined by model variable block 312 and is dimensionless (unitless). The user has inadvertently made a mistake in the specification of the units of the constant "1." This type of inadvertent units error is a common occurrence in drug model construction and can lead to significant delays in model verification.

At a later time, the user connects the output of the expression block 304 with the volume input of a central compartment block 316. The equations generator 128 creates the equation corresponding to the user-specified model connection, and the units tracker 152 checks for incompatible units. In this case, the units are incompatible, and an error message is generated. In one embodiment, the error message is immediately displayed on the drug model itself in a small error message frame 320 in proximity to the port associated with the assignment side of the generated equation. Alternatively, the error message is displayed in an error message window, or the like.

In addition to the small error message frame 320, a small units data frame 324 may be displayed in proximity to the output port just connected by the user. In addition, in one embodiment, a block properties window 328 is automatically opened, showing the properties of the block having the output port just connected by the user. The block properties window 328 shows the units data for any constants contained therein, and allows the user to modify units definitions.

The methods just described for units tracking and notification apply equally to the case where units data has not yet been specified. For example, if the user would like the volume of the central compartment block 316 to be random, the user would create a continuous distribution block and wire its output to the left-side volume port the central compartment block 316. As soon as this is done, an error message is generated because the output of the continuous distribution block was not specified as being in units of liters. The small error message frame 320 would appear as before, and in one embodiment, the small units data frame 324 would be displayed and would show that the output of the continuous distribution block is unitless (dimensionless).

In one embodiment, this units tracking1 is performed using a single multi-dimensional data type, or unit type. Every numeric variable and constant (i.e. every numeric term) is defined by this single multi-dimensional unit type, and these unit types are propagated and tracked in every expression. The dimension type for each term in an expression is represented as a matrix, which is a unit type specification. In one embodiment, dimensionless terms have no matrix associated with them. Each dimension corresponds to a physical concept of measurement. For each dimension, there is a set of specific unit names. Each matrix includes a set of unit name specifications and a set of integer exponents. The number of dimensions being tracked determines the size of these two sets.

In one embodiment, there are five basic dimensions of physical units: (1) volume, (2) weight, (3) time, (4) amount, and (5) age. A variable may have a unit type specification that comprises any subset of these dimensions, including all five, or none at all. For example, a variable representing concentration would have units of amount divided by volume, and would thus have a unit name specification and an integer exponent for two dimensions, while the remaining three dimensions would have NULL values. If a variable has a NULL value for each dimension in its unit type, this represents a unitless quantity, and the variable is dimensionless. Additionally, in one embodiment, the integer exponents range from −3 to +3.

The specific unit names for the volume dimension are "L", "dL", "cL", "mL", "nL", "pL", "pint", and "floz", which correspond to liters, deciliters, centiliters, milliliters, nanoliters, picoliters, pints, and fluid ounces respectively. The specific unit names for the weight dimension are "kg" and "lb", which correspond to kilograms and pounds respectively. The specific unit names for the time dimension are "h", "d", "m", and "s", which correspond to hours, days, minutes and seconds respectively. The specific unit names for the amount dimension are "t", "g", "mcg", "ng", "pg", "oz", and "iu", which correspond to arbitrary amount units, grams, micrograms, nanograms, picograms, ounces and international units respectively. The specific unit names for the age dimension are "y" and "wk", which correspond to year and week respectively.

The unit type of a variable, constant or expression is defined using a unit expression. The specific unit names are combined into unit expressions by means of the following unit operators: "*", "/", "(..)", and "1." For example, {L/h/kg} is a unit expression meaning liters per hour per kilogram of body weight, and {1/d} is a unit expression meaning 1 per day. Different units of the same dimension can be added, even if they have different specific unit names, and the software automatically converts the specific unit types as necessary, based upon known relationships between the specific unit names. For example, 1 {d}+6 {h} equals 30{h}.

When two expressions are added, subtracted, or compared, if they are of unlike dimensions, a warning is generated. When two expressions are multiplied or divided, their dimensions are also multiplied or divided. For example, if A is a variable having the dimension of drug amount, and V is a variable having the dimension of volume, then the expression A/V has the dimension of amount/volume, or concentration.

In one embodiment, each dimension has default units, which the user may specify, and each unit type specification comprises a conversion factor and an exponent array. For example, if the default units are {mL}, {kg}, {d}, {mcg}, {wk}, then the term "0.6 {mcg/mL}" is parsed into the number 0.6 and a unit type specification of [(1), (−1,0,0,1, 0)]. But the term "60 {mcg/L}" is parsed into the number 60 and a unit type specification matrix of [(0.001, (−1,0,0,1,0)]. Additionally, the term "6" is parsed into the number 6 and a unit type specification matrix of [(1), (0,0,0,0,0)], which means that this constant is dimensionless. Thus, in this embodiment, each unit expression may be thought of in parsing terms as a variable value and a data type array, wherein the value is a conversion factor, and the array is a set of exponential powers.

In accordance with this embodiment, unit expressions are converted into matrices that function both as unit definitions for unit checking and as conversion factors. All the unit names can be used in unit expressions, regardless of what the default unit names are, because they actually contain the conversion constants. This is only true, however, for those situations in which the conversion constants are known. For example, in one embodiment, conversion between milligrams and international units is not always possible because the definition of an international unit depends upon information that may not be available, such as the molecular weight of the drug molecule or the number of active binding sites. In one embodiment, if a particular conversion constant is unknown, a conversion constant of 1 is assumed, and a message is generated to warn users not to mix particular units.

FIG. 4 is a table showing primitives for an internal parse tree data structure for use in translating model blocks into equations according to one embodiment. Column 402 contains the names of the primitives, and column 404 contains a brief description of each primitive. Although multiple internal formats are possible, a parse tree data structure is considered preferable. Parse tree data structures are well understood in the software compiler arts, and thus additional description of the data structure is not provided herein.

With regard to terminology, a closed form machine is a small block of memory comprising two arrays of equal length. The two arrays store A values and α values for the equation:

$$\sum_{i=1}^{K} A_i e^{(\alpha_i t)} \quad (1)$$

Thus, in one embodiment, K is 5, and each closed form machine is a two by five array storing ten values. Closed form machines are used with a procedure for calculating closed form solutions in the generated high-level language source code. Thus, primitives such as InitCF and CloneCF involve memory allocation for each new closed form machine in the generated code. For example, the code for an effect compartment block attached to a central compartment block with a closed form solution is generated by allocating space for a new closed form machine, copying the values of the closed form machine for the central compartment into the new closed form machine, and then modifying the new closed form machine values accordingly.

Figure 5:
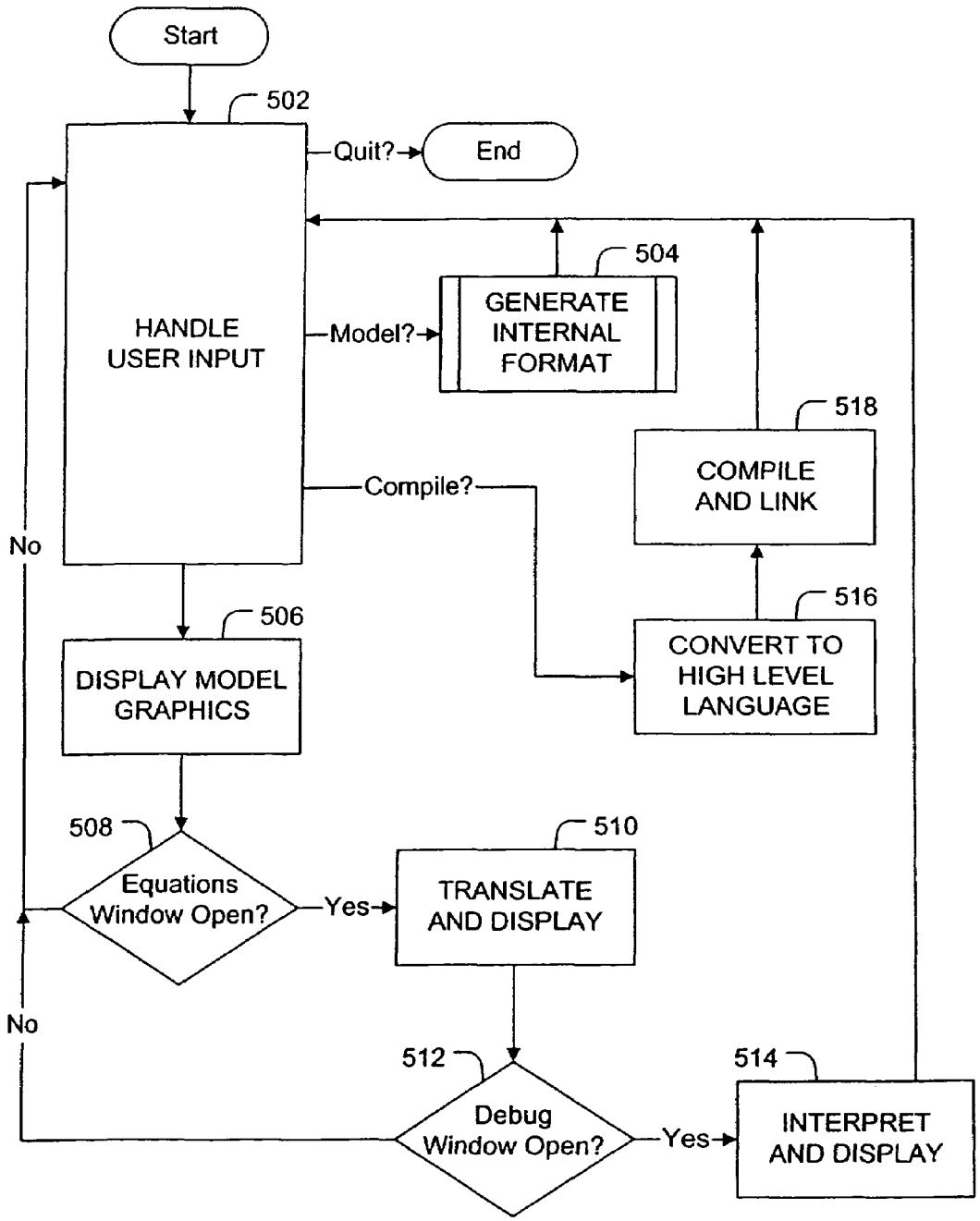
FIG. 5 is a flowchart depicting a process for providing an interactive graphical drug model editor according to one embodiment.

FIG. 5 is a flowchart depicting a process for providing an interactive graphical drug model editor according to one embodiment. The process begins with step 502, in which user input is handled. Step 502 represents all the various functionality of the graphical user interface discussed above. Thus, it includes opening new windows, selecting menu options, selecting icons for placing blocks on the screen, etc. For example, if a "quit" menu option is selected, the process ends.

Additionally, step 502 handles "save" and "load" options. For example, if a "save" option is selected, the current graphical model is stored in the model library 148. Likewise, if a "load" option is selected, a graphical model may be loaded from the model library 148. In one embodiment, the "save" and "load" options are implemented with a library window. Thus, drug models, or portions of them, can be transferred between the library window and the drug model construction window 104 by drag-and-drop or by cut-and-paste.

If a user performs a model construction action, such as placing a block or connecting two blocks, the process moves to step 504, which is a defined process step. In defined process step 504, an internal format, such as the internal parse tree data structure discussed above, is generated. In one embodiment, this internal format is the only data structure used to represent the drug model as it is constructed.

In order to avoid name change problems, block ports (variables) are encoded in a particular fashion, in one embodiment. In the internal parse tree, every variable is a port of a block, and is represented by a 32-bit identifier consisting of a 16-bit block number concatenated with a 16-bit port number. Blocks are numbered starting with 0 for the first block. A block number of −1 is used to signify global variables such as the time variable T. On a real block (numbered 0 or more), the input ports are numbered starting at 0, up through 15, and the output ports are numbered starting at 16 up through 31. Ports are not given names until they are translated into the visible surface syntax or converted to Fortran. Thus, port names can be readily changed by the user without invalidating the generated code.

The defined process step 504 is described in greater detail below in connection with FIG. 6. Following defined process step 504, the process returns to step 502.

Periodically, the process moves from step 502 to step 506. In step 506, the internal format is traversed, and the bocks and wires of the graphical model being constructed is rendered. In one embodiment, this graphical rendering of the model is painted onto a visible screen bitmap. In an alternative embodiment, the graphical model is rendered to an offscreen bitmap, which is then swapped with an on-screen bitmap, so as to avoid flicker. This rendering is performed typically at a rate of five times per second, so as to give an illusion of continuous motion.

Following step 506, a check is made in step 508 as to whether an equations window is open. If not, the process returns to step 502. If an equations window is open, control passes to step 510, in which the internal format is translated into the visible surface syntax and displayed in the equations window. Thus, the displayed equations, which represent the constructed drug model, change in real-time as the drug model is constructed. The visible surface syntax and the equations window are discussed in greater detail below in connection with FIG. 7B.

Following step 510, a check is made in step 512 as to whether a debugging window is open. If not, the process returns to step 502. If a debugging window is open, control passes to step 514, in which the internal format is interpreted with the simulation interpreter 144. The simulation interpreter 144 treats the internal format as a scripting language subroutine representing the drug model. Under the control of the debugging window of the drug model editor, the statements in internal format are executed by the simulation interpreter 144 to simulate the time course of individual subjects.

In one embodiment, the simulation utilizes a Second-Order Runge-Kutta algorithm to solve the differential equations by numerical integration. In the process, warning messages are accumulated and made available to the user, so that he/she may correct the model. The simulation determines the time varying behavior of variables of interest, which have been selected by the user, within the drug model, and this time varying behavior is displayed in the debugging window. The debugging window and its functionality are discussed in greater detail below in connection with FIG. 7C.

Following step 514, control passes back to step 502. Once the user is satisfied with the drug model, the user may select a compile option within step 502. If the user selects the compile option, control passes to step 516. In step 516, the internal format is converted into a high-level language such as Fortran. In one embodiment, step 516 is performed by a separate program module, such as the code generator 140. However, in another embodiment, the code generator 140 and the equations generator 128 are both part of a single code generation module that performs three main functions: (1) translation from drug model blocks into the internal parse tree data structure, (2) translation from the internal parse tree data structure into the visible syntax language, and (3) translation from the internal parse tree data structure into Fortran source code.

In one embodiment, all the variables created in the model are global variables in the resulting high-level language source code, and the code produced in step 516 is all located within a single subroutine. Variable names are generated in part using the unique block numbers. Thus, each variable is assigned a name that will not conflict with any previously assigned variable name. This holds true even if the user is modeling two drugs, and thus there are two sets of compartments.

The conversion of step 516 is straightforward given the nature of the internal format. However, one area of interest is the implementation of the differential equations. The usual way to solve a set of ordinary differential equations (ODE) is to use numerical integration. If there are any differential equations, this is determined in step 516, and a derivative subroutine is created having all the sorted statements. The derivative subroutine is used with a general purpose ODE algorithm, such as Runge-Kutta-Fehlberg or Gear's Stiff.

In one embodiment, step 516 also includes a check for whether solving by matrix exponent is possible. This check is performed first, since the method of matrix exponent has higher performance and stability. Only if the matrix exponent method does not work, is numerical integration used. The check is performed by attempting to generate code to set up the matrix. If the matrix setup code is successfully generated, then a general matrix exponent algorithm is used with the matrix in the generated high-level language source code. The following pseudo-code shows an example method for setting up the matrix:

---

Subroutine: SetupMatrixForExponent:

---

Setup a list of variables to be treated as if they were constants, such
    as subject covariates and infusion rate variables.
We will be creating a square matrix M, and an expression to
    compute each element of the array. Where N is the number of
    integrator variables, the matrix will have N+1 rows and N+1
    columns.
comment: fill in columns 1 through N with the rate terms.
for J = 1 to N begin
    Let Y be the Jth integrator variable
    for I = 1 to N begin -continued

```
Subroutine: SetupMatrixForExponent:
    Let X be the Ith integrator variable
    Let R be dX/dT, i.e. the right hand side of X's
        differential equation.
    Let Q be dR/dY, evaluated symbolically by
        manipulating R.
    If Q is constant, as determined by examining it for
        variables, then M(I,J) = Q
    Otherwise, the subroutine returns the value false
        because matrix exponent cannot be used.
    end
    Let M(N+1,J) = 0
end
comment: fill in column N+1 with the infusion terms.
for I = 1 to N begin
    Let X be the Ith integrator variable
    Let R be dX/dT, i.e. the right hand side of X's differential
        equation, including the infusion rate term.
    Let Q be R, evaluated with all integrator variables equal to
        zero.
    If Q is constant, as determined by examining it for
        variables, then M(I,N+1) = Q
    Otherwise, the subroutine returns the value false because
        matrix exponent cannot be used.
end
Let M(N+1, N+1) = 0
```

Figure 7A:
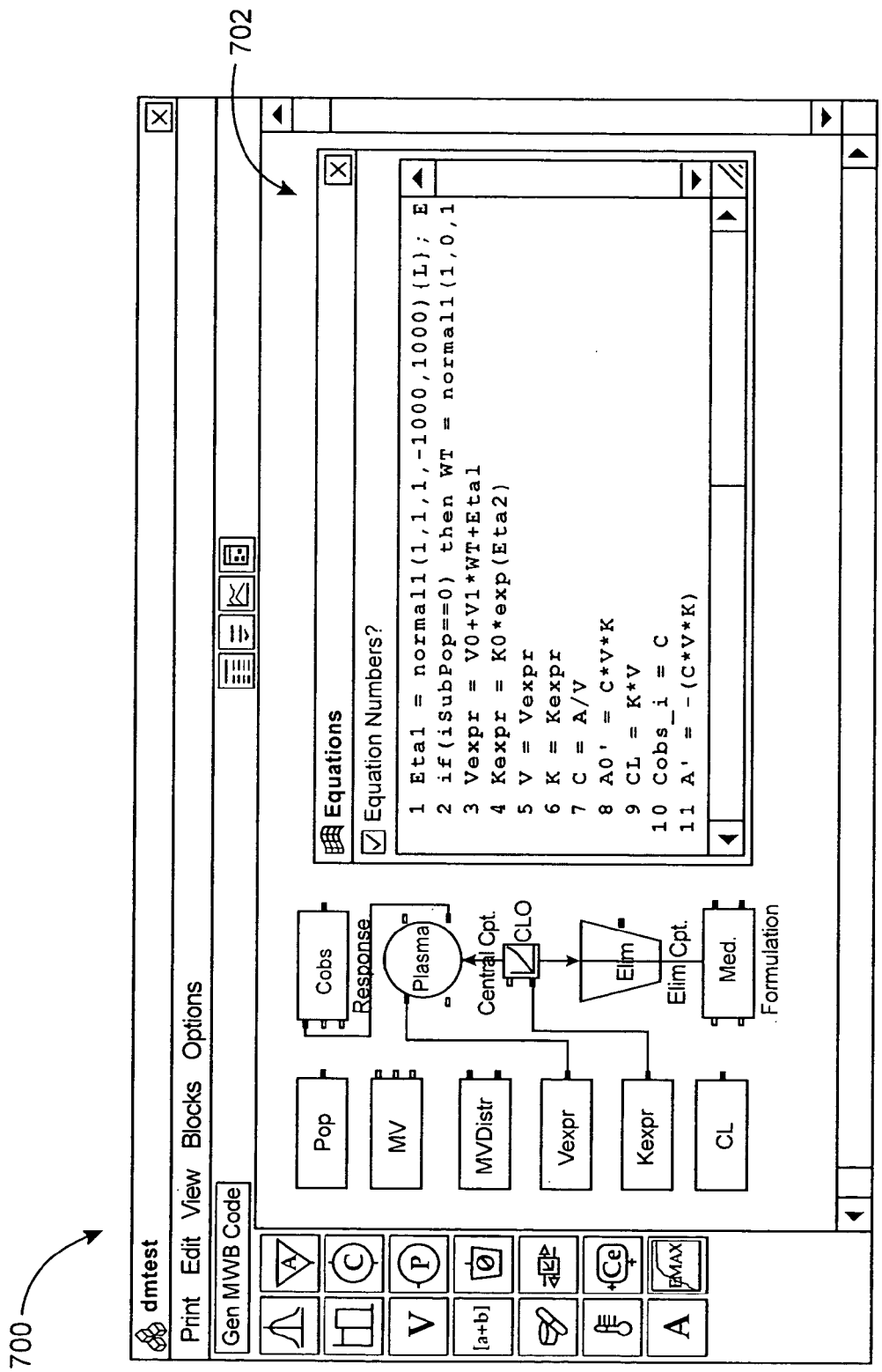
FIG. 7A is an illustration showing an exemplary drug model construction window and an exemplary drug model equations window according to one embodiment.

To further illustrate step 516, reference is now made to FIG. 7A, which is an illustration showing an exemplary drug model construction window and an exemplary drug model equations window according to one embodiment. The drug model construction window 700 displays a simple drug model. The drag model equations window 702 displays the equations for the simple drug model. In an embodiment where only the numerical integration method is used, the generated Fortran subroutine is as follows:

```
subroutine zzDerivative(zzNInteg, t, zzInteg, zzRate)
    use zzglobals
    use zzunits
    implicit none
    integer zzNInteg
    double precision t
    double precision zzTemp(30) ! expression stack
    double precision, target :: zzInteg(*)
    double precision, target :: zzRate(*)
    double precision, pointer :: A
    double precision, pointer :: A_RATE
    double precision, pointer :: A0
    double precision, pointer :: A0_RATE
    A => zzInteg(1)
    A_RATE => zzRate(1)
    A0 => zzInteg(2)
    A0_RATE => zzRate(2)
c   C = A/V
    zzTemp(1) = A
    zzTemp(2) = V
    zzTemp(1) = zzTemp(1)/(zzTemp(2) + 1d-30)
    C = zzTemp(1)
c   A' = (C*V*K)
    zzTemp(1) = C
    zzTemp(2) = V
    zzTemp(1) = zzTemp(1) * zzTemp(2)
    zzTemp(2) = K
    zzTemp(1) = zzTemp(1) * zzTemp(2)
    zzTemp(1) = -zzTemp(1)
    A_RATE = zzTemp(1)
    A_RATE = A_RATE + PlasmaIRate
c   A0' = C*V*K
    zzTemp(1) = C
    zzTemp(2) = V
    zzTemp(1) = zzTemp(1) * zzTemp(2)
    zzTemp(2) = K
    zzTemp(1) = zzTemp(1) * zzTemp(2)
    A0_RATE = zzTemp(1)
    A0_RATE = A0_RATE + A0_IRATE
end
```

In an embodiment, wherein matrix exponent solutions are enabled as discussed above, the generated subroutine is:

```
subroutine zzInitializeMatrix(zzIErrCode, zzMat)
    use zzglobals
    use zzunits
    implicit none
    integer zzIErrCode
    double precision zzMat(3,3)
    double precision zzTemp(30) ! expression stack
c   zzMat(1,1) = -(K*(V*(V/(V*V))))
    zzTemp(1) = K
    zzTemp(2) = V
    zzTemp(3) = V
    zzTemp(4) = V
    zzTemp(5) = V
    zzTemp(4) = zzTemp(4) * zzTemp(5)
    zzTemp(3) = zzTemp(3) / (zzTemp(4) + 1d-30)
    zzTemp(2) = zzTemp(2) * zzTemp(3)
    zzTemp(1) = zzTemp(1) * zzTemp(2)
    zzTemp(1) = -zzTemp(1)
    zzMat(1,1) = zzTemp(1)
c   zzMat(2,1) = K*(V*(V/(V*V)))
    zzTemp(1) = K
    zzTemp(2) = V
    zzTemp(3) = V
    zzTemp(4) = V
    zzTemp(5) = V
    zzTemp(4) = zzTemp(4) * zzTemp(5)
    zzTemp(3) = zzTemp(3) / (zzTemp(4) + 1d-30)
    zzTemp(2) = zzTemp(2) * zzTemp(3)
    zzTemp(1) = zzTemp(1) * zzTemp(2)
    zzMat(2,1) = zzTemp(1)
c   zzMat(3,1) = 0
    zzTemp(1) = 0d0
    zzMat(3,1) = zzTemp(1)
c   zzMat(1,2) = 0
    zzTemp(1) = 0d0
    zzMat(1,2) = zzTemp(1)
c   zzMat(2,2) = 0
    zzTemp(1) = 0d0
    zzMat(2,2) = zzTemp(1)
c   zzMat(3,2) = 0
    zzTemp(1) = 0d0
    zzMat(3,2) = zzTemp(1)
c   zzMat(1,3) = 0
    zzTemp(1) = 0d0
    zzTemp(1) = zzTemp(1) + PlasmaIRate
    zzMat(1,3) = zzTemp(1)
c   zzMat(2,3) = 0
    zzTemp(1) = 0d0
    zzTemp(1) = zzTemp(1) + A0_IRATE
    zzMat(2,3) = zzTemp(1)
c   zzMat(3,3) = 0
    zzTemp(1) = 0d0
    zzMat(3,3) = zzTemp(1)
    end ! subroutine
```

Referring again to FIG. 5, following step 516, the generated high-level language source code is compiled and linked with appropriate software in step 518. For example, in one embodiment, the generated high-level source code is a Fortran subroutine that models a drug. This Fortran subroutine is compiled and linked with a drug trial simulator. In this embodiment, all of the variables are global variables. Thus, they are readily accessible by the trial simulator source code. The trial simulator code knows how to handle these global variables because the protocol in the trial simulator knows about the treatment and observation/response blocks (and also the covariates of the population block). Thus by wiring the rest of the constructed drug model into the treatment and observation/response blocks, the user has specified the interface between the generated drug model source code and the trial simulator source code.

Following step 518, the process returns to step 502. In an alternative embodiment, there is no step 518. In this embodiment, only the source code for the drug model subroutine is created. The user must then independently compile and link the drug model subroutine with whatever other source code is being used.

With regard to the trial simulator source code, in one embodiment, the drug model editor is coupled with a trial simulation designer. In this embodiment, the user designs both the drug model and the protocol for use in a simulated drug trial. In some instances, it is necessary to perform a simulation on the assumption that a patient has been receiving medication for a "long time" and has reached some form of steady-state. This situation is handled by generating Fortran code to produce this simulation by simulating the subject for a length of time on a repetitive dosing regimen for a sufficient length of time prior to the start of the formal treatment regimen. This generated Fortran code considers only those integrator variables that contribute to an observable response. The generated Fortran code simulates repetitive dosing until the values of those integrators has changed by no more than a set percentage from one dosing event to the next. If there are multiple dose events to be applied repeatedly, having different inter-dose intervals, the longest interval is used.

Figure 6:
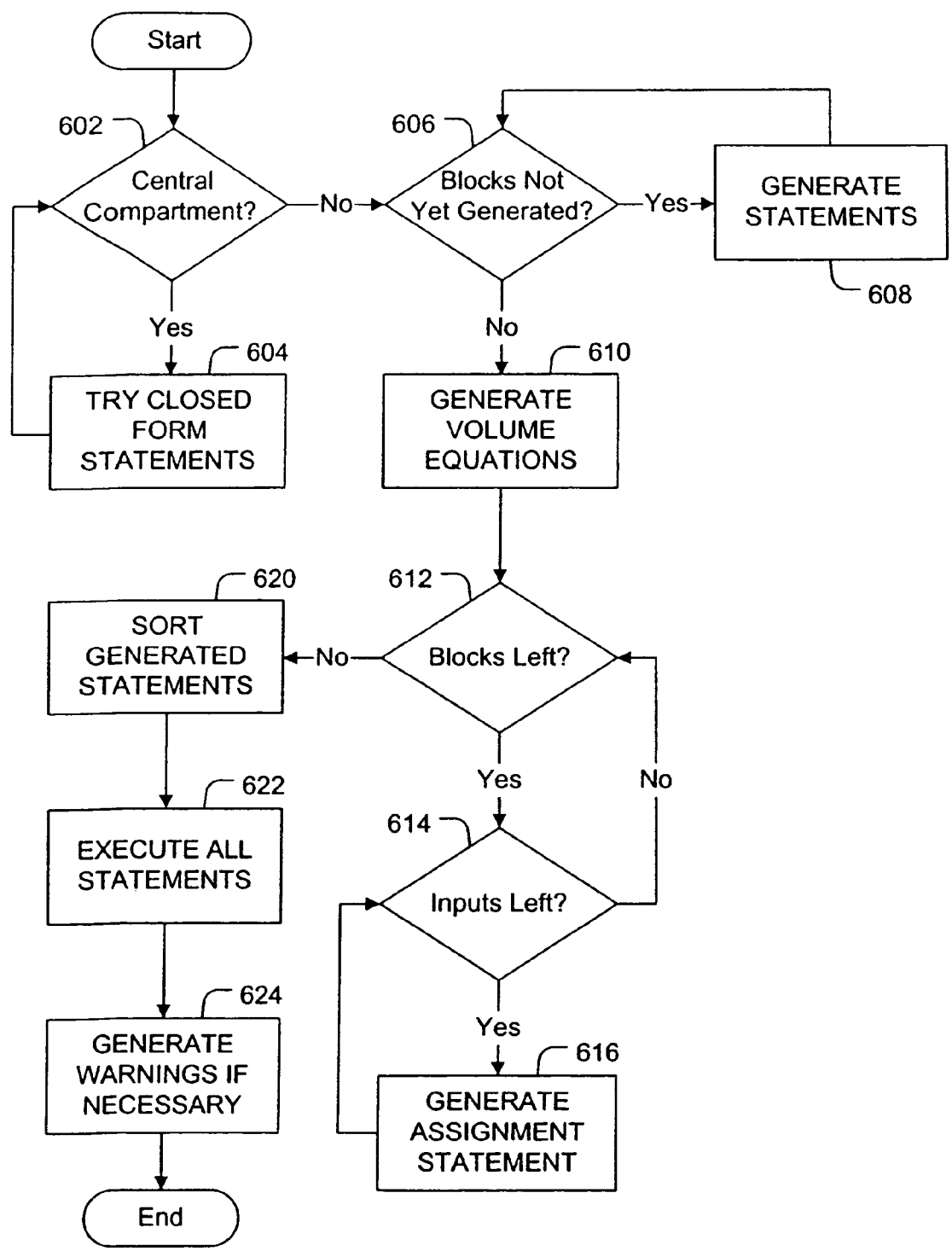
FIG. 6 is a flowchart depicting a process for translating model blocks into an internal format according to one embodiment.

FIG. 6 is a flowchart depicting a process for translating model blocks into an internal format representative of the defined process step 504 from FIG. 5. The process begins with step 602, in which a check is made if there are any central compartments that have not yet been considered. If so, for each central compartment, control passes to step 604, in which any possible closed form solutions are generated. A check is made as to whether a closed form solution is possible and closed form statements are generated in the internal format. The following pseudo-code shows an example method for implementing step 604:

Subroutine: TryGenClosedFormStatements
    Get the list of compartments and flows connected to this central compartment
    There must be 1 central compartment and 1 elimination compartment, no non-linear flows, no more than 2 peripheral compartments, no more than 1 absorption compartment, and every peripheral, or absorption compartment must be free of other flows. It can have any number of effect compartments.
    If these conditions are not met, then closed form generation fails for this central compartment.
    Create an InitCF parse tree node.
    If the elimination flow is parameterized by micro parameters, provide that parameter as an argument to the InitCF.
    If the elimination flow is parameterized by clearance, provide that parameter, divided by the volume of the central compartment, as an argument to the InitCF.
    Do likewise for each peripheral flow attached to the central compartment.
    Output the InitCF statement.
    If there is an absorption compartment, generate a Add1stOrdInputCF statement, using the rate constant of the absorption flow.
    for each effect compartment attached to the central compartment,
        Generate a CloneCF statement to make a copy of the central compartment closed form machine.
        Generate a Add1stOrdCF statement to convolve it with the effect compartment delay.
        Generate a GetValCF statement to read the closed form machine.

Once all the central compartments have been considered, control passes from step 602 to step 606. In step 606, a check is made as to whether there are any blocks for which internal format has not yet been generated. If so, for each such block, control passes to step 608, in which the appropriate statements and/or differential equations are generated. The following pseudo-code shows an example method for implementing step 608:

Subroutine: GenBlockStatements
    Generate statements and/or differential equations (SetDerv) for the given block:
    Compartment: GenCmptStatements
    Effect Compartment: gen $C(0)=IC$; $C'=(I-C)*K$
    Integrator: gen $O(0)=IC$; $O'=I$
    Continuous distribution: gen IfLevel(V=CDistr . . . )
    Categorical distribution: gen IfLevel(V=DDistr . . . )
    Discrete Effect: gen IfLevel(V=DLogit . . . )
    Choose, Adder, Multiplier: gen code as appropriate.
    Expression: gen V=user code expression
    New Procedure:
        Gen initialization statements for integrators.
        Gen initialization statements for the procedure variables.
        Gen the user-code body statements.
        Gen SetDerv statements for the differential equations.
    Actions At Times: gen code as appropriate.
    Delay, Table, Exponentiation, Ln, Square, SquareRoot, Inverse: gen code as appropriate.
    Linear, Structural parameter: gen code as appropriate.
    Emax, Indirect: gen code as appropriate.
    Event: gen code as appropriate.
    Population/Multivariate distribution: gen code as appropriate.
Subroutine: GenCmptStatements:
    Given a particular compartment,
    Start building a differential equation for the amount of drug in the compartment.
    for each flow block attached to this compartment,
        Generate the forward flow rate expression, depending on the parameterization of the flow and the compartments.
        Append this expression to the differential equation, with a minus sign.
        Generate the reverse flow rate expression, (if any) and append it to the differential equation, with a plus sign.
    Generate a statement to set the initial amount of drug in the compartment.

Once all the remaining blocks have been considered, control passes from step 606 to step 610. In step 610, any necessary volume equations are generated. In the case that a central compartment has a volume parameter, and any peripheral compartment has a volume parameter, and the flow between them has micro-constant parameters, then the volume of the peripheral compartment is determined by the other parameters. Thus, for example, if a central compartment is compartment one and an attached peripheral compartment is compartment two and the flows between compartments one and two are expressed as micro-constants, an internal format statement is generated in step 610 to calculate the volume of the peripheral compartment. This internal format statement expresses the equation V2=V* K12/K21, where V2 is the volume of compartment two, V1 is the volume of compartment one, K12 is the micro-constant flow from compartment one to compartment two, and K1 is the micro-constant flow from compartment two to compartment one.

Following step 610, step 612 begins a new loop through each of the blocks. A check is made in step 612 as to whether any blocks are left. For each block, control passes from step 612 to 614. In step 614, a check is made as to whether any inputs are left. For each input for the current block, control passes from step 614 to step 616. In step 616, an assignment (SetPort) statement corresponding to the sum of wires coming into the port is generated. Once all the blocks and ports have been looped through, control passes from step 612 to step 620.

In step 620, all of the generated internal format statements are sorted into dependency order. In one embodiment, step 620 comprises placing all statements in an unsorted group, then transferring the statements into a sorted group one by one, where the transfer order is the execution sequence. Each statement is transferred only after all the variables it requires to do any calculation expressed in the statement are already calculated in statements in the sorted group. Certain variables are assumed to already be calculated in statements in the sorted group from the beginning. These assumed variables include integrators and any population block covariate. The following pseudo-code shows an example method for implementing step 620:

Subroutine: SortGeneratedStatements:
    The generated statements are sorted in order of dependency.
    First certain variables are marked as defined: T, all free parameters, all integrator variables, all population covariates, all model variables, and all formulation and response values.
    Then all statements are moved to a temporary array, from which we will move them back to the main statement array.
    do until no more statements can be moved
        find a statement such that all variables appearing in its expressions are defined.
        Move that statement back into the main statement array.
        If such a statement cannot be found, exit this loop.
    If any statements remain in the temporary array
        Issue a warning that there may be a circular dependency.
        Copy the remaining statements into the main array.

In an alternate embodiment, statements are transferred from the unsorted group to the sorted group as late as possible.

Following step 620, all statements are executed unconditionally by the interpreter in step 622. This execution propagates unit dimensions to identify inconsistent units. Thus, all statements are executed regardless of the state of conditional statements, such as if-then-else tests. If any inconsistent units are discovered in step 622, this causes warnings to be generated in step 624 before the process ends.

FIG. 7B is an illustration showing an exemplary drug model equations window for the drug model shown in FIG. 2A. An equations window 730 displays equations derived from the drug model for review by the user. The internal format statements are displayed in the equations window 730 in the visible surface syntax. Each statement has a number 732 by which it can be referenced from the messages window 116. Differential equations 734 are shown in the form V'=rate-expression. This form of display is very useful as a way of verifying the drug model because it is a simple way of modeling time varying behavior.

Figure 7C:
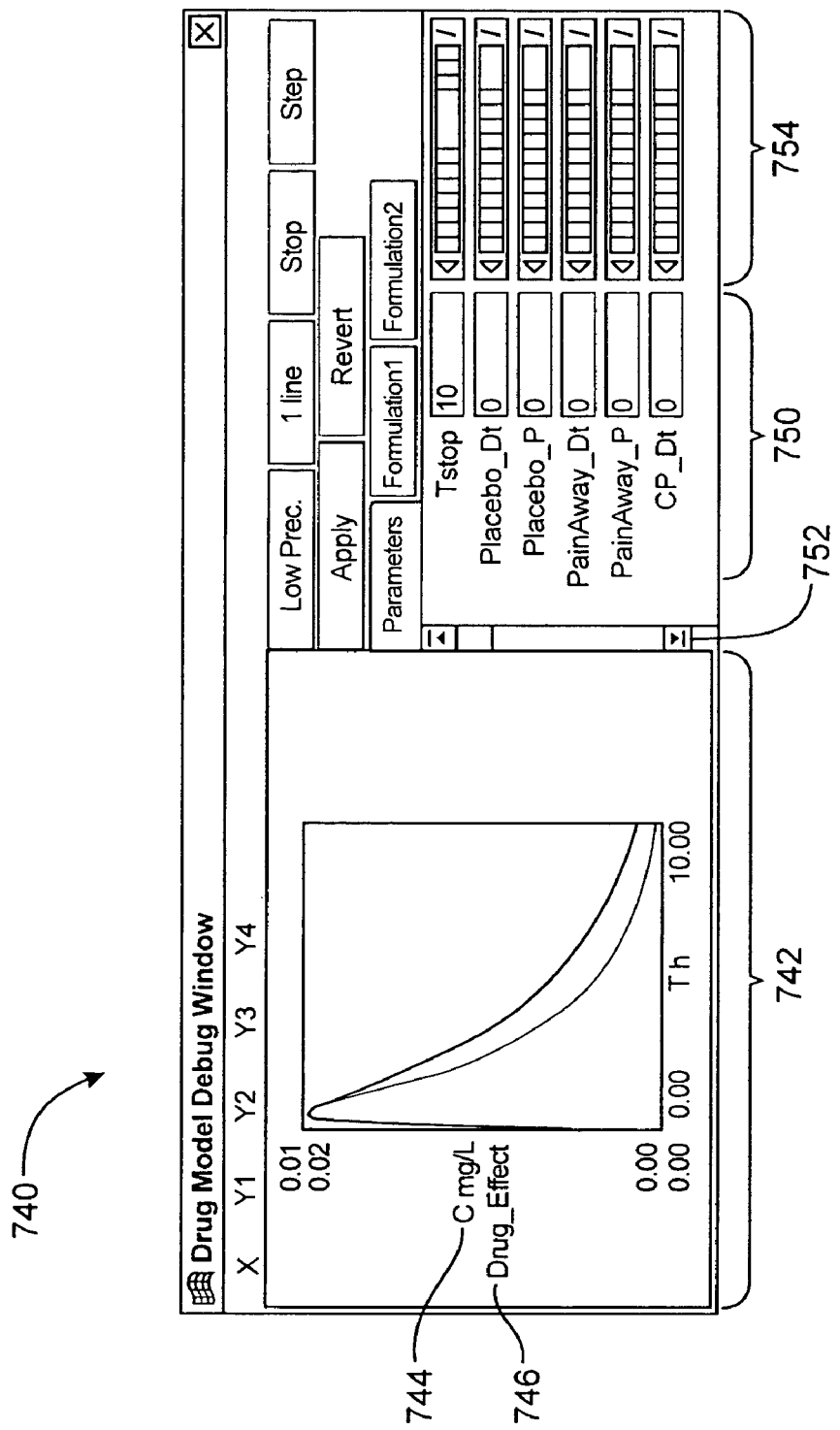
FIG. 7C is an illustration showing an exemplary drug model debug window for the drug model shown in FIG. 2A.

FIG. 7C is an illustration showing an exemplary drug model debug window for the drug model shown in FIG. 2A. A debug window 740 presents an interface in which the model can be executed interactively and various numerical quantities can be plotted against time or against each other in real time, while allowing various parameters of the model to be modified interactively. Thus, for example, a graphing portion 742 of the debug window 740 can be used to graph a concentration output 744 from the response block CP in FIG. 2A and a drug effect output 746 from the Drug_Effect emax block in FIG. 2A as a function of time.

The various parameters of the drug model, and their current values, are displayed in a parameters portion 750 of the debug window 740. Additional parameters can be viewed by moving the parameter scroll bar 752. Note that the debug window 740 employs the dynamic graphical interface discussed in connection with FIG. 2B, thus if the debug window 740 is resized, the parameter scroll bar 752 adjusts accordingly and disappears if all the parameters can fit into the parameters portion 750 of the debug window 740.

The values for the various parameters can be changed by entering new values in the value field of the parameters portion 750, or by clicking the arrow icons or clicking and dragging the wheel adjuster in the value adjustment portion 754 of the debug window 740. Whenever an adjustment is made to one of the parameters, the graph in the graphing portion 742 of the debug window 740 is updated substantially immediately thereafter. In one embodiment, this graph update is accomplished automatically because the graph is continuously being updated by active interpretation of the internal format statements by the simulation interpreter 144, even when the parameters remain unchanged.

The graphing functionality includes plotting compartmental amounts against time, under bolus or infusion doses, plotting with repetition, and plotting on semilog axes. The interactive graphing functionality allows the user to readily verify the behavior of the drug model vis-à-vis expectations and to adjust parameters to check for reasonable values. In Emax components, effect E can be plotted against concentration C to verify the emax curve and EC50. Indirect models can be plotted against time to verify expected behavior. Distributions can be visualized by plotting the random values against time, or in a histogram. Multivariate distributions can be visualized by plotting the random variables against each other.

Figure 7D:
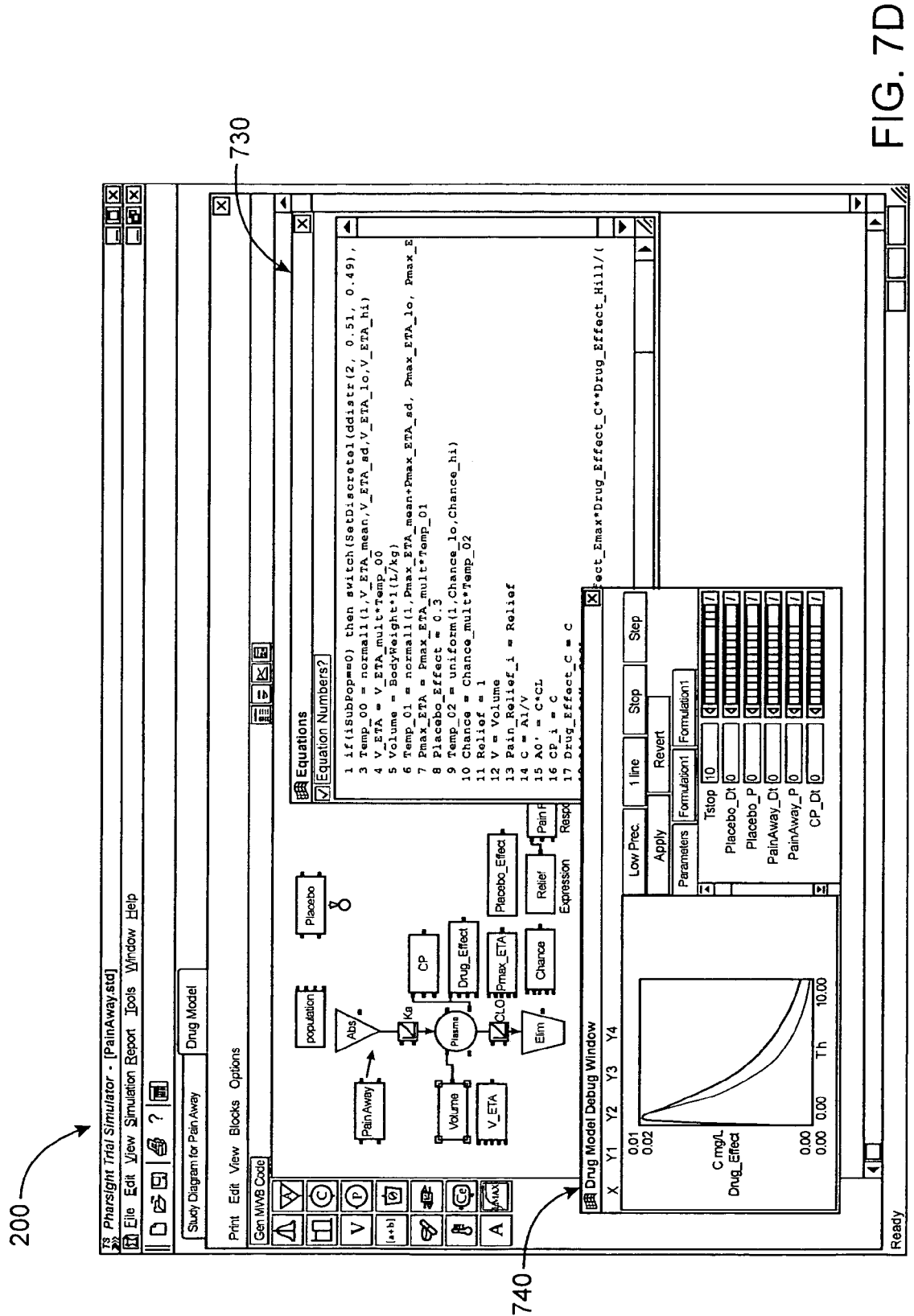
FIG. 7D is an illustration showing an exemplary drug model construction window, an exemplary drug model equations window and an exemplary drug model debug window according to one embodiment.

FIG. 7D is an illustration showing an exemplary drug model construction window, an exemplary drug model equations window and an exemplary drug model debug window according to one embodiment. The drug model construction window 200 is the same as that from FIG. 2A, the drug model equations window 730 is the same as that from FIG. 7B, and the drug model debug window 740 is the same as that from FIG. 7C. As can be seen from FIG. 7D, a user may open all of these windows simultaneously. When the user modifies the graphical drug model in the drug model construction window 200, the equations in the drug model equations window 730 and the plots in the drug model debug window 740 are updated substantially immediately thereafter.

Figure 8:
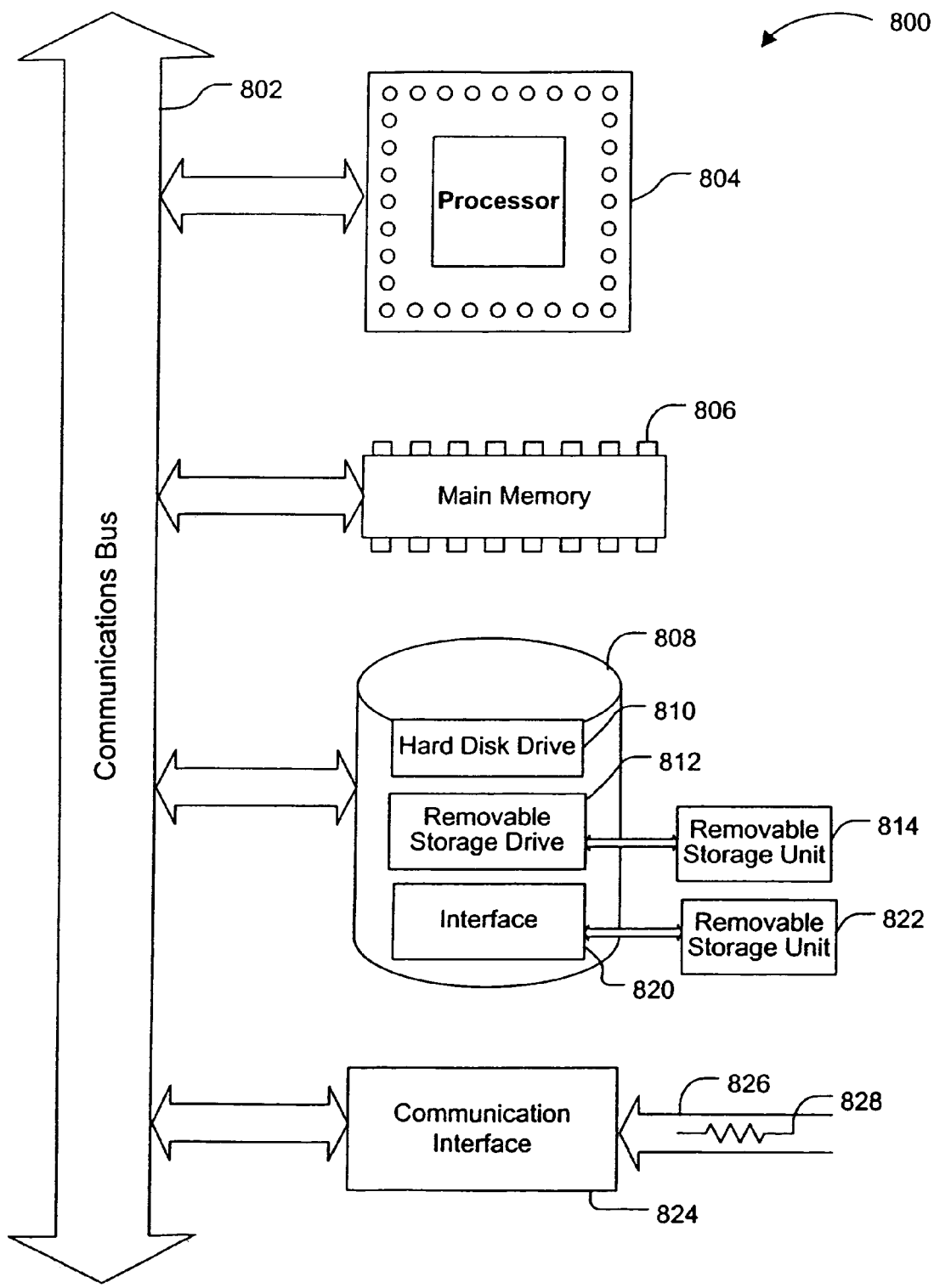
FIG. 8 is a block diagram illustrating an example computer system in which elements and functionality of the invention are implemented according to one embodiment.

FIG. 8 is a block diagram illustrating an example computer system in which elements and functionality of the invention are implemented according to one embodiment. The present invention may be implemented using hardware, software or a combination thereof and may be implemented in a computer system or other processing system. An exemplary computer system 800 is shown in FIG. 8. Various software embodiments are described in terms of this exemplary computer system 800. After reading this description, it will become apparent to a person having ordinary skill in the relevant art(s) how to implement the invention using other computer systems and/or computer architectures.

The computer system 800 includes one or more processors, such as processor 804. Additional processors may be provided, such as an auxiliary processor to manage input/output, an auxiliary processor to perform floating point mathematical operations, a digital signal processor (a special-purpose microprocessor having an architecture suitable for fast execution of signal processing algorithms), a back-end processor (a slave processor subordinate to the main processing system), an additional microprocessor or controller for dual or multiple processor systems, or a coprocessor. It will be recognized that such auxiliary processors may be discrete processors or may be built in to the processor 804.

The processor 804 is connected to a communication bus 802. The communication bus 802 may include a data channel for facilitating information transfer between storage and other peripheral components of the computer system 800. The communication bus 802 further provides the set of signals required for communication with the processor 804, including a data bus, address bus, and control bus (not shown). The communication bus 802 may comprise any known bus architecture according to promulgated standards, for example, industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and the like.

Computer system 800 includes a main memory 806 and may also include a secondary memory 808. The main memory 806 provides storage of instructions and data for programs executing on the processor 804. The main memory 806 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), and ferroelectric random access memory (FRAM).

In one embodiment of the computer system 800, the main memory 806 is a combination of a RAM and a read only memory (ROM), and the secondary memory 808 is not present.

The secondary memory 808 may include, for example, a hard disk drive 810 and/or a removable storage drive 812, representing a floppy disk drive, a magnetic tape drive, an optical disk drive, etc. The removable storage drive 812 reads from and/or writes to a removable storage unit 814 in a well-known manner. Removable storage unit 814, represents a floppy disk, magnetic tape, optical disk, etc., which is read by and/or written to by removable storage drive 812. As will be appreciated, the removable storage unit 814 includes a computer usable storage medium having stored therein computer software and/or data.

In alternative embodiments, secondary memory 808 may include other similar means for allowing computer programs or other instructions to be loaded into the computer system 800. Such means may include, for example, a removable storage unit 822 and an interface 820. Non-limiting examples of such include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage units 822 and interfaces 820, which allow software and data to be transferred from the removable storage unit 822 to the computer system 800.

Computer system 800 also includes a communications interface 824. Communications interface 824 allows software and data to be transferred between computer system 800 and external devices, networks or information sources. Examples of communications interface 824 include a modem, a network interface (such as an Ethernet card), a communications port, a PCMCIA slot and card, etc. Communications interface 824 preferably implements industry promulgated architecture standards, such as Ethernet IEEE 802 standards, Fibre Channel, digital subscriber line (DSL), asymmetric digital subscriber line (ASDL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), Data Over Cable Service Interface Specification (DOCSIS), and so on.

Software and data transferred via the communications interface 824 are in the form of signals 828, which can be electronic, electromagnetic, optical or other signals capable of being received by communications interface 824. These signals 828 are provided to communications interface 824 via a channel 826. This channel 826 carries signals 828 and can be implemented using wire or cable, fiber optics, a phone line, a cellular phone link, a radio frequency (RF) link, infrared interface (IR) or other communications channels.

Computer programming instructions (also known as computer programs, software or code) are stored in the main memory 806 and/or the secondary memory 808. Computer programs can also be received via the communications interface 824. Such computer programs, when executed, enable the computer system 800 to perform the features of the present invention as discussed herein. In particular, the computer programs, when executed, enable the processor 804 to perform the features and functions of the present invention. Accordingly, such computer programs represent controllers of the computer system 800.

In one embodiment, the communications bus 802 is coupled with a display (not shown), such as a cathode ray tube (CRT), for displaying information to a computer user. Various input devices may also be coupled with the communications bus 802 for communicating information and command selections to the processor 804. These input devices may include a keyboard (not shown), a cursor control (not shown), such as a mouse, trackball, or cursor direction keys, and a microphone (not shown) for voice command inputs.

As used herein, the term "computer readable medium" refers to any media used to provide one or more sequences of one or more instructions to the processor 804 for execution. Non-limiting examples of these media include removable storage units 814 and 822, a hard disk installed in hard disk drive 810, a ROM installed in the computer system 800, and signals 828. These computer readable media are means for providing programming instructions to the computer system 800.

In a software-implemented embodiment, the software may be stored in a computer readable medium and loaded into computer system 800 using hard drive 810, removable storage drive 812, interface 820 or communications interface 824. The software, when executed by the processor 804, causes the processor 804 to perform the features and functions of the invention as described herein.

As noted above, it is also possible to implement embodiments of the invention using a combination of both hardware and software. It should be appreciated that modification or reconfiguration of the computer system 800 of FIG. 8 by those skilled in the relevant art(s) will not depart from the scope or teachings of the invention.

This disclosure is supplemented by the following article entitled *Differential Evaluation: a Cache-based Technique for Incremental Update of Graphical Displays of Structures*, written by Michael R. Dunlavey, and published in Software—Practice and Experience, Vol. 23(8), pp. 871–893 (August 1993).

Differential Evaluation: a Cache-based

Technique for Incremental Update of

Graphical Displays of Structures

Michael R. Dunlavey

Performance Software Associates, Inc.,

276 Harris Avenue, Needham Mass. 02192, U.S.A.

SUMMARY

Many applications of graphical man-machine interfaces require incremental update of to image, with controllable time granularity, having multiple views of the Information, generated by modular, maintainable software having minimal resource overhead. A technique called differential evaluation is presented that addresses these needs. Instead of driving the display from a data structure, it uses an ad hoc display procedure in conjunction with a FIFO cache to generate and maintain the display. Maintaining displays of variable structure is accomplished through the use of conditional mechanism in the display procedure. The technique has been extended to meet many different needs, such as the use of graphic contexts, display of overlapping objects, double-buffering, and a variety of user input schemes. The efficiency of the technique, in time and storage, permits its use with modest equipment. It has been used for several years in a number of industrial user interfaces.

KEY WORDS Graphics interfaces Incremental display Differential evaluation

INTRODUCTION

In human-computer interfaces in industry, a ubiquitous problem is to maintain incrementally updated displays of dynamically changing information. The content of the displays is often graphical, containing pixel-based primitives such as lines and polygons, as well as textual data. The speed of the display hardware is often constrained by limited communications bandwidth. In industrial settings, the variety and complexity of displays tends to be much higher than in research settings. The importance of accuracy can also be higher, as for example in air traffic control. The result is that software engineering issues, such as reliability and development cost, assume high importance. All of these concerns add up to a significant problem domain that has only recently been appreciated in the literature.[1]

PROBLEM STATEMENT

Following Reference 1, the problem can be characterized by the need for incremental redisplay, temporal granularity, efficient access, multiple views and modularity, as explained below.

Incremental Redisplay

In many applications, it is infeasible to regenerate the entire display after every change to the underlying data, owing to the speed of hardware and/or communications.

One possible approach would be to require application programmers to add code to detect changes to data and trigger update of portions of the screen. However, this leads to exceedingly non-modular source code due to the display-support functionality being interwoven with the application.

Another approach would be to use a powerful workstation as the remote display device, download a remote data structure to it, and let it regenerate the display at high speed. However, that only alters the problem to one of keeping the remote data structure up to date, which still must be done incrementally. In addition, it has the disadvantage of needing additional special-purpose code to run on the remote workstation, plus host-computer bookkeeping of the remote data structure.

Temporal Granularity

Temporal granularity of updating a display refers to the degree to which the underlying data can be changed before an update is necessary. For example, a text editor could implement the replacement of text as deletion followed by insertion. A simple approach to display maintenance might update the display after each operation, but that would result in excessive screen activity. In general, it is desirable to update the display at arbitrarily spaced points in time rather than immediately after each lowest-level update to the information structure, i.e. to have coarse temporal granularity.

The key to achieving coarse temporal granularity is to make a distinction in data structure between what graphics are on the screen and what are wanted on the screen. If this distinction is not made, then each change to the data structure must be accompanied by an immediate change to the image.

Efficient Access

It is important not to impose display-related constraints on an application. For example, a process-control algorithm could update underlying data many times per second, and it is important that this be efficient and not encumbered by the need to simultaneously update a display.

Multiple Views

A given display may contain multiple representations of the same underlying data. This is a complication for display-update schemes that have screen objects linked to underlying data objects.

Modularity

It is important to keep a separation in program source code between the underlying application and the human interface. This is because each of these undergo separate functional modifications, and it would complicate the maintenance if each small change in display requirements forced many different pieces of code to change within the application.

Related Work

Although the problem of incremental update of displays is widespread, it is underrepresented in the literature. One promising approach[1] is to use an ItemList structure, which is a list structure representing graphical objects. Each graphical object has a version history, so that what is on the screen is represented along with what is wanted. Incremental update is accomplished by checking for newer versions of each object. The versions also permit an undo capability, useful in editors. In applications where the underlying application-specific data structure is not an ItemList, this approach leaves open the question of how the ItemList gets constructed and incrementally maintained. One approach[2] involves the use of a declarative description of structured views, so that the dependencies between application data and display-related data can be deduced.

The problem of incremental update of multiple views of structured data has been addressed in the field of algorithm animation,[3] in which the approach has been event-driven, without addressing the temporal granularity issue.

THE TECHNIQUE

The technique presented here, differential evaluation, uses a compiled display procedure (Diagram 1), which is an application-specific procedure to paint a static view of some application data by calling primitives to draw lines, text, and so on. Even though the display procedure describes a static view, it will be used to produce a dynamic view by executing it multiple times. Efficiency is achieved by avoiding unnecessary redrawing at the primitive level.

The display procedure is executed once to show the initial display, and once again each time the display is to be updated. On the second and subsequent executions, differences are detected at the level of individual graphical primitives, which are redrawn only if necessary. To do this, there must be a memory of the parameters of all graphical primitives from the prior execution, and this is provided in the form of a common FIFO[4] acting as a "delay line" memory. The technique relies on the chronological sequence of primitives being repeatable, which is true except for the complicating effect of conditional statements in the display procedure. Conditional statements are handled by a general mechanism.

The FIFO, although it contains the parameters of primitive objects such as lines and text, is not a "display list" in the usual sense. First, it contains no object type information and no segmentation; it is nonsense to any program other than the display procedure that generated it. Secondly, its contents have a very specific meaning: they represent the parameters of the primitives that are visible at present, as opposed to what is desired to be visible. The only time they are used graphically is to erase things, not to draw them.

Comparing this technique to the ItemList structure of Reference 1, the display procedure takes the place of both the ItemList structure's most recent version and procedural dependencies used to build/modify it. To represent what is actually visible, differential evaluation uses the contents of the FIFO, and the ItemList uses its second most recent version. To accomplish major structural changes to the display, differential evaluation intercepts the conditional statements, such as IF and FOR, in the display procedure, whereas the ItemList structure makes use of deletion markers on objects.

A Simple Example

Consider a simple display illustrated in Diagram 2. The underlying data consists of a single variable n that is incremented before each update of the display. The display

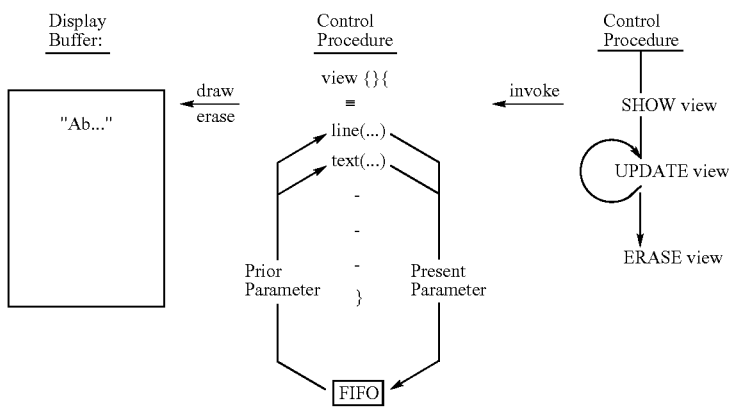

Diagram 1: Incremental update of graphical display by differential evaluation. The display procedure is differentially evaluated under control of the control procedure to draw/erase graphics in the display buffer. The FIFO cache contains exactly the parameters of visible objects plus control information. SHOW mode disables output from the FIFO, and ERASE mode disables input to the FIFO.

views the value of n in a variety of ways. First there is a string "HELLO" n' whose position varies as a function of n, and which is only visible when n is odd. Secondly, there is a tabular fist of strings 'N is n now', where the length of the table depends on n. Whenever the user strikes a key, the value of n is incremented and the display is updated, making it consistent with the new value of n.

The application-specific programming required to support this display is given below. It consists of a display procedure called view( ) and a control procedure called main( ).

```
int n = 0;
  view( ) {
    int I;
    /* describe the location, visibility,
       and content of "Hello . . ." */
    IF (n % 2)
      CALL(text,(9 – n % 10, n % 10, "HELLO %d", n));
    END
    /* describe the group of strings "N is n now" */
    FOR(i = 0, i < (n % 5). i++)
``` a)

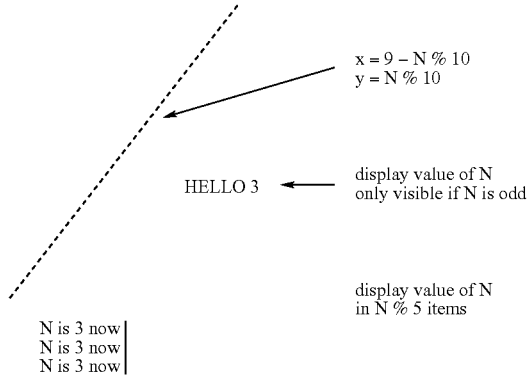

```
b) int N;
   view( ) {
     int j;
     IF(N % 2)
       CALL(text.(9–M%10, N%10, "HELLO %d",N));
     END
     FOR(I=( ), i<(N%5), i++)
       CALL(text,(0,10+i,*N is %d now*,N));
     END
```

Diagram 2: A simple display and its display procedure

```
            CALL(text,(0, 10 + I,
              "N is %d now", n))'
            END
          }
       main( ){
         mode = SHOW;
         view( );
         mode = UPDATE;
         while(getchar) != 'q'){
           n++;
           view( );
         }
         mode = ERASE;
         view( );
       }
```

The procedure view( ) is written in a special universal language that is presented here as a subset of C,[5] augmented with macros. The purpose of this procedure is to encode the desired appearance of the display. The behavior of the view( ) procedure is determined by a global variable, the mode, having one of three values: SHOW, UPDATE, and ERASE.

The way view( ) is used to first invoke it in SHOW mode to paint the initial image, then invoke it in UPDATE mode every time an incremental update of the image is desired, and finally invoke it in ERASE mode to erase the image.

ERASE mode is symmetrical to SHOW mode. However, in sonic cases it may be simpler to just clear the display surface and the FIFO.

Such a technique requires memory of what is on the screen. This is provided by the FIFO cache, in which the parameters of graphical objects are stored. The principal innovation of this technique is its extension to handle conditionals, such as the IF and FOR statements, such that it can be used to maintain displays of arbitrary structural complexity.

Ordinarily, such a technique might be considered inefficient because it traverses the entire display procedure whenever it performs an update. However, the simplicity of the technique and the fact that the display procedure is compiled result in such rapid execution that in most cases is competitive with other schemes.

Explanation

Diagram 3 illustrates the basic operation of the technique. Each graphical primitive, such as a line or a text, follows the same pattern. In SHOW mode it draws graphics on the screen and puts its parameters in the FIFO. In UPDATE mode it not only puts its parameters in the FIFO but gets its previous parameters out of the FIFO. Since the previous parameters represent its current visible appearance, it can determine if its appearance needs to be incrementally updated. Symmetrically, in ERASE mode, it gets its previous parameters from the FIFO and uses them to erase itself from the display. Various techniques for erasing things are explained below under "Overlapping objects".

The operation of the IF conditional statement, which always has a matching END, is illustrated in Diagram 4. The sequence of statements between the IF and the END is called the "body" of the IF statement. The meaning of the IF statement is that the graphic objects specified in the body are to be visible if and only if the IF test expression is True at the time the display is updated. Therefore, if the test expression changes from False in the previous invocation to True in the current invocation, the body must be executed in SHOW mode so as to become visible. Symmetrically, if the test expression changes from True to False, the body must be executed in ERASE mode to make it invisible. Either way, the mode change is temporary because the END statement restores the mode to what it was before the IF statement was entered. Since the body can contain further nested IF statements, or can execute subroutines containing IF statements, arbitrary structures can be traversed, and views of them maintained. This can only work if the contents of the FIFO remain synchronized with the state of the display procedure, and there is a proof that it does, provided that a certain discipline is followed. This discipline is explained below under "Robustness".

Implementations of this technique can be extremely tiny, as shown in Diagram 5.

To maintain sets of similar objects in the display, such as multiple lines in a scrolling text display, or multiple piece parts on a conveyor line, or multiple aircraft in a traffic display, an interaction capability is needed. An example is "FOREACH aircraft A, it is visible at location XY(A)".

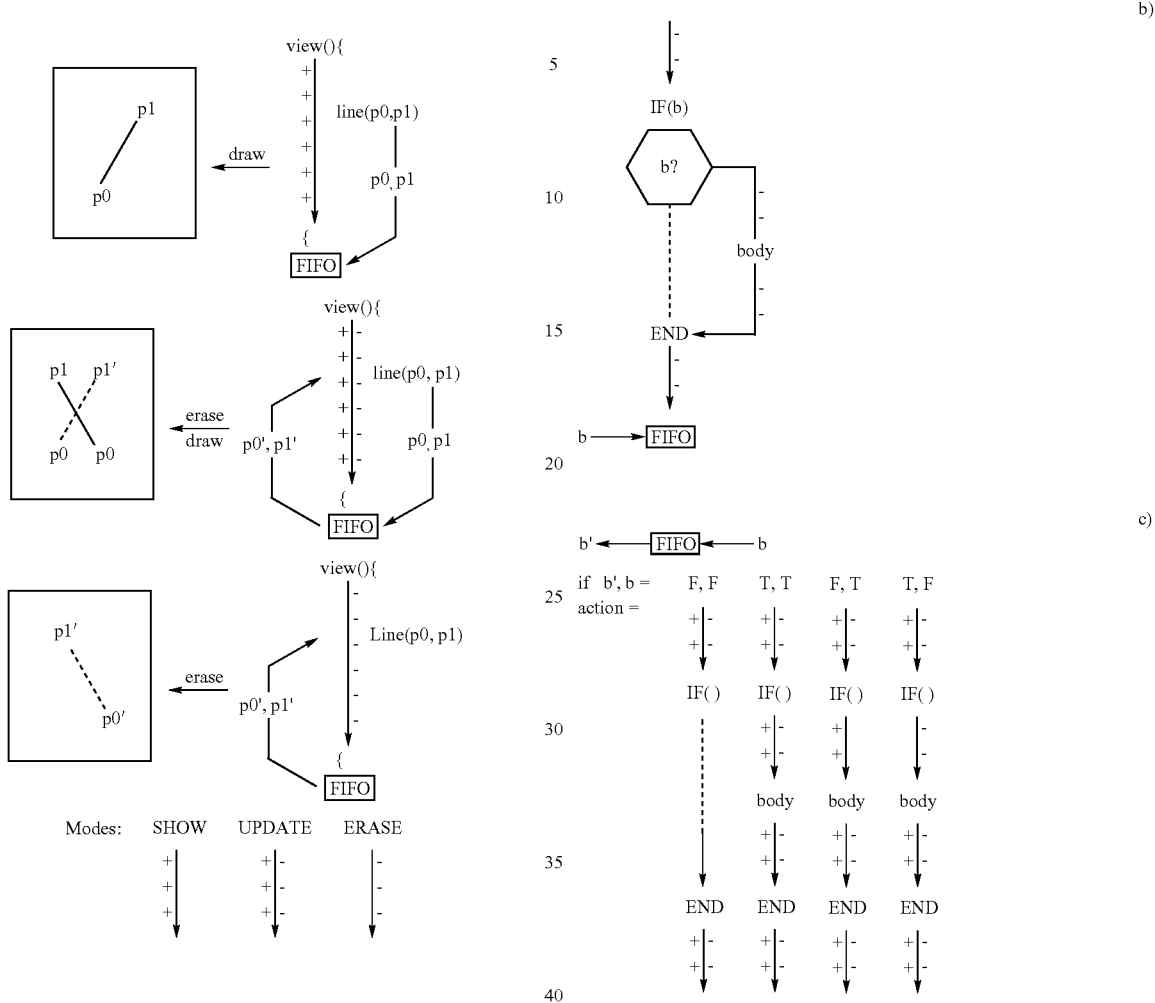

Diagram 3: Maintenance of a line segment. In SHOW mode (a) the line is drawen and its end points written to the FIFO. In UPDATE mode (b) the new end points are written, and the past end points are read from the FIFO. If different, the line segment is graphically updated. In ERASE mode (c), the past end points are read and the line segment is erased.

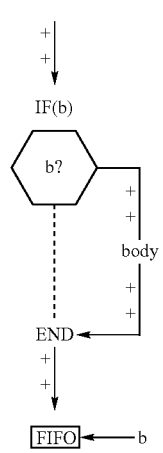

Diagram 4: Operation of the IF-END pair of statements. The IF statement reads and writes the boolean value of its test expression in the FIFO, exactly as if it were a graphical primitive. (a) In SHOW mode, the body is executed if the test is True. (b) In ERASE mode, the body is executed if the past value of the test is True. (c) In UPDATE mode, there are four cases as shown. A transition in the truth value of the test expression results in the body being performed in SHOW or ERASE mode.

Iteration is provided by a FOR-END pair of statements, patterned after the construction in C. If the number of objects to be displayed dynamically changes, the proper number of them are shown or erased so as to keep the display correct. Since a FOR statement is functionally identical to an arbitrarily nested set of IF statements, the implementation is very simple. The behavior of the FOR statement, although correct, can be counterintuitive. For example, if the FOR statement is displaying an array of objects A, B, and C, and object A is removed, the FOR statement behaves as if object C were removed while objects A and B were only renamed. More intelligent iteration statements have been implemented, able to detect insertions/deletions in the middle of a list, not just at its end. However, to present them is beyond the scope of this paper.

```
/* A very Minimal implementation in C */
/* Note: "get" and "put" refer to FIFO operations */
enum (SHOW, UPDATE, ERAZE) mode;
#define X(expr)(mode!=ERASE ? (expr): 0)
#define IF(b)(int m1=mode; if(ifutil(X(b)&&1))(
#define FOR(a,b,c)(int m1=mode; for(X(a);ifutil(X(b)&&1);X(c))(
#define END } mode=m1;)
#define CALL(f,args)(mode!=ERA.SE ? (f args) : (f( )))
int ifutil(b) int b;(
    int b1;
    switch(mode) (
    case SHOW: putInt(b); return b;
    case UPDATE: putInt(b); getInt(&b1);
        if (b= =b1) return b;
        mode - (b ? SHOW : ERASE); return 1;
    case ERASE: getInt(&b1); return b1;
    )}
/* Etremely Crude but Concise Primitives
void text(x,y,format,args) int x,y; char (format; int args; (
    int   * a = &args
    int   x1,y1;
    char buff[100], bufl[100];
    if (mode!=ERASE)
        sprintf(buf,format,a[o],a[1],a[2],a[3],a[4],a[5]);
    switch(mode) {
    case SHOW: putInt(x); putInt(y); putStr(buf);
        settextposition(x,y); outtext(buf);
        break;
    case UPDATE: putInt(x): putInt(y); putStr(buf);
        getInt(&x1); getInt(&y1); getStr(bufl);
        if (x= =x1 && y= =y1 && stromp(buf,buf1)= =0) return;
        settextposition(x1,y1); outblanks(strlen(buf1));
        settextposition(x,y); outtext(buf);
        break;
    case ERASE: getInt(&x1); getInt(&y1): getStr(buf1);
        settextposition(x1,y1); outblanks(strlen(buf1));
    }}
void line(u,v,x,y) int u,v,x,y;(
    int u1,v1,x1,y1;
    switch(mode)}
    case SHOW: putInt(u), putInt(v); putInt(x); putInt(y);
        draw__line(u,v,x,y);
        break;
    case UPDATE:
        putInt(u); putInt(v); putInt(x); putInt(y);
        gatInt(&u1); getInt(&v1); getInt(&x1); getInt(&y1);
        if (u= =u1 && v= =v1 && x= =x1 && y= =y1) return;
        erase__line(u1,v1,x1,y1);
        draw__line(u,v,x,y);
        break;
    case ERASE:
        getInt(&u1); getInt(&v1); getInt(&x1); qetInt(&y1);
        erase__line(u1,v1,x1,y1);
    )}
```

Diagram 5: A very minimal Implementation in C

Since the IF-END construct is a single-branch conditional, it is natural to consider a two-branch conditional, IF-THEN-ELSE. No IF-THEN-ELSE statement has been implemented, partly because it is not so simple, but mainly because SWITCH, patterned after switch in C, is more general, for example, these two pieces of code are functionality equivalent:

```
if(test)                         switch(test){
{                                    default:
        AAAAA1-                              AAAAA;
{                                            break;
else {                               case FALSE.
        BBBBB;                               BBBBB;
{                                    {
```

In UPDATE mode the logic of a SWITCH statement is to perform its body either once, if the test value has not changed, or twice: ERASEing with the old test value, and SHOWing with the new test value. Its implementation as a C macro is rather complex and is omitted.

Viewing Tree Structures

A good test problem for any incremental display update technique is the display of tree-structured data[3] during algorithm animation. An image of a binary tree can be maintained by the following display procedure:

```
struct node {
    int value;
    struct node *left, *right;
    } * ptop;
view( ){
    CALL(tree__view,(ptop,320,0,320,10,166));
    }
tree__view(p.x0.y0,x,y,dx) struct node *p;{
    IF(p && dx >= 10)
        CALL(line,(x0,y0,x,y));
        CALL(text,(xy, "%d",p->value));
        CALL(tree__view,(p->left,x,y,x-dx,y+10,dx/2));
        CALL(tree__view,(p->right,x,y,x+dx,y+10,dx/2~);
        END
    }
```

In this display procedure, tree_view( ) is a recursive subprocedure for displaying the subtree pointed to by ρ. If ρ is NULL, nothing is visible. Also, if this node is so deep in the tree that the nodes would be too close together (dx<10) the subtree is not visible.

view(p,x0,y0,x,y,dx) Struct node 'p; {
IF(p)

a)
```
        CALL (line, (x0, y0, x, y));
        CALL (text, (x. y. "%d", ρ->value));
        CALL (view, (p -left. x, y.x-dxy+20.dxJ2));
        CALL (view, (p ->right, x, y, x-+dx, y+20, dxt2));
        END
    }
```

-continued

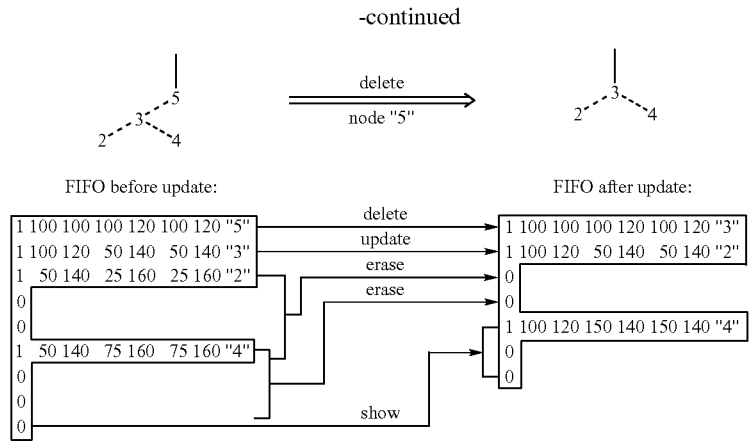

b)

Diagram 6. Update of an image of a binary tree data structure. The recursive part of the display procedure is given in (a). In (b) there is a four-node binary tree image and its corresponding FIFO. After deleting the topmost node, the display procedure is invoked once in UPDATE mode, producing the resulting image and its FIFO. The correspondence between the two FIFOs is shown - The 0 and 1 values are the IF test values. Transitions of these values result in erasing and drawing of substructures.

Otherwise, the display of the subtree consists of a line descending to the node, a text string giving the value of the node, and two recursive subtrees. Dynamically, if a particular pointer ρ is set to a non-NULL value between invocations, the IF statement ensures that its subtree will be shown. Symmetrically, if ρ becomes NULL, its subtree will be erased. If only the value of the node changes, then only its printed value will be updated. The process is illustrated in Diagram 6.

It is important to note that the value of ρ itself is not necessarily tracked. For example, it may be that an entire subtree is detached from one place in the tree and inserted at another. To the given display procedure this is not seen as a portion of the display changing location. Rather it is seen as a shrinkage in one part of the tree and an unrelated growth in another. The result is valid, although it may seem counterintuitive.

EXTENSIONS

The implementation given above is in its most minimal form, for ease of exposition, but it is easily extended and modified to meet various needs.

Graphic Contexts

Graphical systems ordinarily provide a complex set of attributes for graphical objects, such as color, line style, line width, font style, and so on.[6] If these were included in the argument list of every graphics primitive, the display procedure would become unwieldy and difficult to maintain. Also, the storage of these arguments in the FIFO, for every graphics primitive, might soon consume prohibitive amounts of storage. The normal practice is, rather than include these attributes in the argument list of every primitive graphical object, to hold their current values in a global record called the "graphic context". These values are then set and modified by separate subroutine calls.

To do the same thing within differential evaluation, it is necessary to maintain two global records instead of one. One is the current graphic context record, and the other, referred to as the "old context", represents the graphic context as it was during the previous invocation of the display procedure. Primitive routines that modify the attributes of the graphic context are extended, under differential evaluation, to modify both records.

To give an example of how this is done, consider a pair of simple graphic context records:

```
    struct context {
        int x,y;
        int color;
    };
    struct context cur, old:
The primitive routines to modify the graphic context are:
    moveto(x,y) int x,y;{
        if (mode==SHOW || mode==UPDATE){
            cur.x = x; cur.y = y;
            enquelnt(cur.x); enquelnt(cur.y);
        {
        if (mode==UPDATE | mode==ERASE){
            dequelnt(&old-x); dequelnt(&old.y);
        {
        }
    setcolor(color) int color;{
        if(mode==SHOW || mode==UPDATE){
            cur.color = color;
            enquelnt(cur.color);
        {
        if (mode==UPDATE || mode ==ERASE){
            dequelnt(&old.color);
        {
    {
```

The primitive line routine becomes a routine of only two arguments, x and y. Its semantics are that there is to be a line segment from the x,y position in the current graphic context to the new x,y position, using the current color. The graphic context is to be updated to the new x,y position. The routine is only a little more complex than before:

```
lineto(x,y) int x,y;{
    int oldx,oldy;
    switch(mode){
    case SHOW:
        enquelnt(x); enquelnt(y);
        draw_line(cur.x,cur_y,x,y,cur.color);
```

-continued

```
        cur.x = x; cur.y = y;
        break;
    case UPDATE:
        enquelnt(x); enquelnt(y);
        dequelnt(&oldx); dequelnt(&oldy);
        if(cur,x!=old.x || cur.y!=old.y
            ||x!=oldx | y!=oldy
            ||cur.color!=old,color
            ({
        erase__line(old.x,old.y,oldx,oldy.old.color)
        draw__line(cur.x,cur.y,x.y,cur.color);
        }
        cur.x = x; cur.y = y;
        old.x = oldx; old.y = oldy;
        break;
    case ERASE:
        dequelnt(&oldx); dequelnt(&oldy);
        erase__line(old.x,old.y,oldx,oldy,old.color)
        old.x = oldx; old.y = oldy;
}}
```

This has the effect of reducing the amount of data stored in the FIFO. Each instance of lineto maintains a line segment having five, integer parameters, but only stores two parameters in the FIFO. If the numbers of moveto and setcolor primitives are minimal, the storage savings are significant.

Overlapping Objects

When two or more graphical objects, such as text-strings or line segments, overlap one another, selective ensure of one may damage the appearance of the others, depending on the method of selective erasure and drawing.

If the method of erasure is to redraw the object in the background color, it will leave holes in the objects that it overlaps. However, in many real-world applications, the data being presented is fixed-format, primarily textual, and does not move. In such cases, objects simply do not overlap because if they did they would hide information. Objects tend not to move, but rather their contents may change. For example, if the display contains two text-strings, text A
text B that are dynamically transposed:

text B
text A this can be easily programmed as two text objects having fixed position and variable content, rather than fixed content and variable position, so they can be updated without damaging one another.

If the method of erasure is to do all drawing and erasing in XOR mode, objects can be moved without permanent damage to other objects. The penalty is that where objects overlap they will be the wrong color. However, in many applications this is acceptable, and nothing more sophisticated is required.

In those applications where opaque objects may overlap and must not damage one another, the differential evaluation technique can be extended to meet the need, at the cost of some complexity. This is done by splitting the UPDATE invocation into two phases, UPDATE1 and UPDATE2, with the intention that all erasing of objects is done in the UPDATE1 phase, and drawing of objects is done in the UPDATE2 phase. It is also necessary to maintain a table of extent records, one record for each visible object, so that damage or possible damage can be detected. Whenever an object is erased in the first phase, and whenever an object is drawn in the second phase, the table is checked, and any overlapping object records are marked as damaged. In the second phase, objects may be drawn either because they are moving, changing color, or becoming visible, or because they have been damaged. Thus, there is a "cascade effect" by which redrawing A damages B, and redrawing B damages C, and so on. The process is not circular because damage to objects drawn earlier in the display procedure need not be repaired, indeed must not be, because that damage is precisely the desired overlap.

The implementation of two-phase update is somewhat more complex, and is detailed in Diagrams 7 and 8. The basic idea is that in the first phase, data obtained from the FIFO is simply fed back into it, with the result that the FIFO is unchanged by the first phase. This allows the second phase to be an exact repeat of the first phase.

There is a problem with this approach, namely that the underlying data must not change between update phases. This is not a problem in applications that are, singlethread, such as computer-aided design (CAD), but it could be a problem in multithread applications such as real-time system monitors. There is a fix for the problem, although it

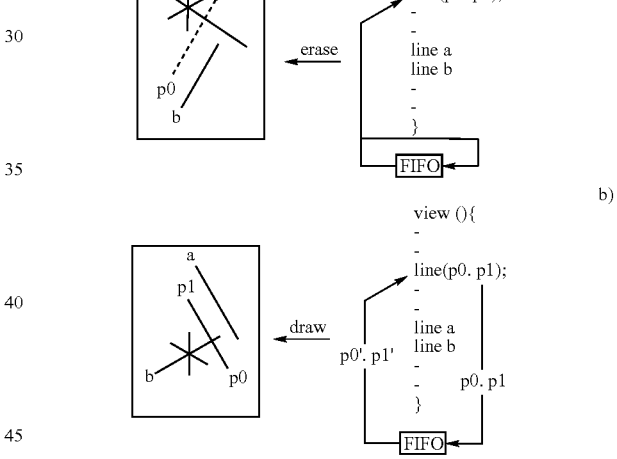

Diagram 7. Handling overlap via two-phase update. In the UPDATE1 phase (a) only the erase part of the graphics isdone, and the past parameters are recycled back into the FIFO. For each line segment in the iamge, there is an extent record with a damage bit. If the erasing damages any other lines (line a), their extent records are so marked, the UPDATE2 phase (b) is like ordinary UPDATE except that no erasing is done. Each line segment is drawn if either its parameters have changed or it has been marked as damaged. Drawing can produce further damage (line b), producing further drawing (lines a and b) so as to restore the overlap.

has never, in fact, been needed. The fix is to use an auxiliary FIFO, called AUX. During phase 1, the present arguments of graphical objects are written to AUX. During phase 2, the present arguments are not evaluated, but are instead read back from AUX. This ensures that the present arguments are identical in both phases. This could be diagrammed as shown in Diagram 9.

Double Buffering

In some applications it is objectionable to do updating, incremental or not, in the visible frame buffer. This gives rise to the "double buffer" technique[7] in which there are two frame buffers, one visible, and one being drawn in. When drawing is complete, the buffers are electronically exchanged for "instantaneous" update.

Ordinarily, the speed at which double buffering can run depends on how quickly the offscreen buffer can be painted. It may be desirable to incrementally update

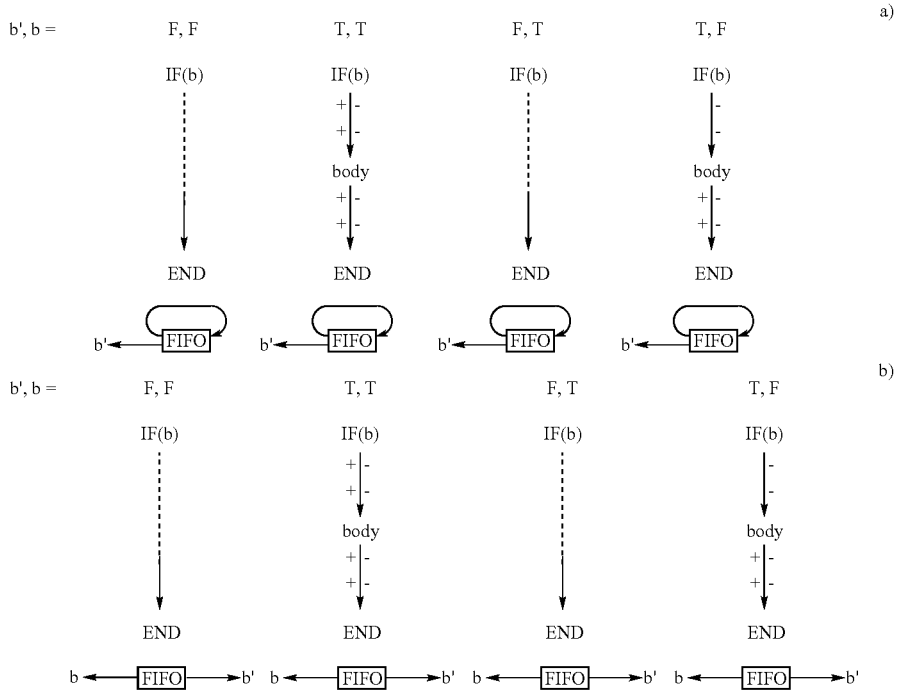

Diagram 8. IF-ENE) processing during two-phase update. In the UPDATE1 phase (a) the past value of the test is recycled into the FIFO. If the body is to be performed in ERASE mode, that is done in the UPDATE1 phase (a). If it is to be performed in SHOW mode, that is done in the UPDATE2 phase (b). Otherwise it is the same as normal IF-END processing.

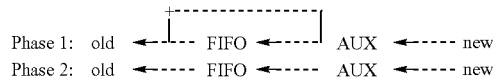

Diagram 9 the offscreen buffer rather than simply repaint it, for performance reasons, and differential evaluation can be extended to do this. In the simplest terms, it is only necessary to start off the process with two SHOW invocations instead of one:

```
mode=SHOW;
view( ); swap_buffers( );
view( ); swap . . . buffers( );
mode=UPDATE;
while( . . . ) {
    view( ); swap_buffers( );
}
mode=ERASE;
view( ); swap_buffers( );
view( ); swap_buffers( );
```

What this is actually doing is maintaining two display surfaces, one in each buffer, and alternating updates between them. By starting with two SHOW invocations, the FIFO contains memory of two displays. Then, during each UPDATE, the data being obtained from the FIFO is the data from the second-to-last invocation, matching the image in the offscreen buffer.

This is a start towards the more general handling of multiple independently updated displays or multiple independent images within a single display. There must be a separate FIFO, mode register and display procedure for each independently updateable image. If object-oriented programming is available, these can be neatly packaged in a class so as to eliminate the global variables.

Combined Example

As an example of overlap handling via two-phase update combined with double-buffering, consider an air traffic display "looking down", so that aircraft at higher altitudes obscure those below. There may be many such displays being shown simultaneously, so it is not desirable to store any display-support information in the aircraft database. For simplicity, assume that an aircraft image is a graphic primitive, represented in the FERO by three numbers (x,y,heading), rather than as a group of line segments. The display procedure says FOR EACH aircraft a, in order by increasing altitude
    display_aircraft(a)

Since in this problem it is desired to use double-buffering, two images will be maintained, one in each buffer. Therefore, there are two sets of data, each containing a FIFO, a mode variable, and an object extent table (for overlap detection).

Assume that there are three aircraft, and that this number does not change; they just move around. Therefore, the size of each FIFO becomes 3 aircraft×4 numbers (x,y, heading, and pointer to extent record)=12 numbers. The size of each extent table is 3 aircraft×5 numbers (min and max x and y, plus damage marker)=15 numbers.

To update a buffer, the display procedure is executed in two phases, UPDATE1 and UPDATE2. In UPDATE1 phase, any aircraft to be moved is erased, and any overlapping extent records are marked as damaged. The FIFO is unchanged. In UPDATE2 phase, any aircraft to be moved is drawn in its new location, and any overlapping extent records are marked as damaged. Any aircraft that is being updated and has not moved will be redrawn if its extent record is marked as damaged, and while it is being redrawn, any overlapping extent records will be marked as damaged. By redrawing things in display-procedure order, the correct back-to-front obscuration is maintained. After the UPDATE2 phase, the FIFO contains the new aircraft locations and headings.

In terms of performance, the basic processing is linear in the number of objects. Assuming that the extent table is organized for efficient look-up, the time spent marking damage is linear in the amount of damage caused when objects are erased and redrawn, which depends on the number of objects being moved and the extent to which they overlap other objects.

This overlap scheme is rather crude. It could be extended to include bounding rectangles in the damage marker, these being used to clip the redraw, so as to minimize damage to other objects.

Temporary Highlighting of Changed Objects

When a display contains a large amount of data, as for example a display of stock quotations, it may be desirable to temporarily change the color of objects when they change value, so as to bring the user's attention to them.

A general solution to this problem is to use the FIFO to make available the prior value of any desired data. For example, if there is to be a bar graph, and the bar should display in red if its height has changed, otherwise green, it could be expressed this way:

int oldht,
    PRIORVAL(barheight, oldht);
    CALL(bar,(x,y,width,barheight/*bar locn, size*/
      ,(barheight==oldht ? GREEN: RED))/*color"/

In other words, set oldht to the prior value of barheight, and let the color of the bar be conditional on both present and prior values. If the prior—prior value were needed, it could be obtained via two calls to PRIORVAL. The implementation of PRIORVAL is a simple matter of storing the new value in the FIFO and retrieving the old:

define PRIORVAL(new.old) priorval(X(new),&(old))

```
void priorval(new,pold) int new, int *pold;(switch(mode){
    case SHOW;
        enquelnt(new);
        *Pold = new; /* 1st time thru, no hilight */
        break;
```

-continued

```
    case UPDATE;
        enquelnt(new);
        dequefnt(pold);
        break;
    case ERASE:
        dequelnt(pold);
}}
```

Generation of Hard Copy

To generate hard copy of an image, a simple method is to institute another mode, namely PRINT mode. In PRINT mode the FIFO is completely ignored and the display procedure simply generates graphics in the usual way, except that they are generated to a print file instead of to the image.

Techniques for Handling User Input

The differential evaluation technique deals only with graphical output. A real user interface requires input as well, so it is valid to see how this could be incorporated.

The technique has been used with a variety of input schemes, keyboard and forms-oriented at one extreme, and mouse-driven at the other. In either case, it is necessary to maintain the existence of input objects that act as the focus for user input. For example, a simple data entry form can contain edit fields as its input objects. A more complex graphical display can contain buttons for triggering actions, sliders for adjusting single variables, or drag points for changing the co-ordinates of items in the underlying data. More complex objects, such as a lasso for encircling things, have been built.

There is nothing unusual about the way these are handled. A data entry field object, for example, is established by a single-line subroutine call in the display procedure, just as any other graphical primitive. In SHOW mode the object is created and displayed, in UPDATE made it is updated, and in ERASE mode it is erased from the screen and then deleted from memory. While it exists, between updates of the entire display, a general event-based input handler can pass keyboard or mouse events to it, and it can update itself on the screen and modify application data.

To clarify this idea a little further, suppose a display is to contain three data-entry fields, supplying data to application buffers a[ ], b[ ], and c[ ]. These fields could be described by three lines in the display procedure:

CALL(text_field,(100,100,a));
    CALL(text-field,(100, 120,b));
    CALL(text-field,(100,140,d));

Each field has an x and y location and a pointer to the application character array to be edited by the user. If a field is to be optional based on other application data, it can simply be placed inside an IF-END construct. If there is to be an array of fields, as in a scrolling region, it could be stated as FOR(i=0, i<n, i++)
      CALL(text_field.(100,100+20*i, buf array[i+first]));
    END Scrolling of the array of fields is accomplished by changing the value of the variable "first" and updating the display.

The implementation of the text-field primitive is given below. In SHOW mode it creates a data-entry field object, displays it, and saves a pointer to it in the FIFO. In ERASE mode, it fetches the pointer to the object from the FIFO and gets rid of it. In UPDATE mode it updates the data entry field, if necessary. The data entry field itself is an object capable of responding to messages such as SHOW, UPDATE, ERASE, MOVE (to move it on the screen), NEWBUF (if its buffer address changes), and CHAR (indicating that a character was typed at it). Object-oriented message passing is indicated below by invoking the object's handler function, passing the object pointer itself as the first argument. (Of course it would be a little cleaner in a true OO language such as C++.)

```
text_field(xy.buf) int x, int y, char *buf;{
    text_field_object_t * p;
    lint x1,y1; char * buf1;
    switch(mode){
        case SHOW:/* allocate, register and show field */
            p = make_text_field_object(x,y.buf);
            register_field(p);
            (*p->func) (p,SHOW);
            putPtr(p); putInt(x); putInt(y); putPtr(buf);
            break;
        case UPDATE:/* if no changes, just update field */
            getPtr(&p) getInt(&x1); getInt(&y1); getPtr(&buf1);
            if (x==x1 && y==y1 && buf==buf1)
                (*P->func) (P.UPDATE);
            else( /* if new location or buffer, handle it */
                if (X!=X1 || y!=y1)
                    (*p->func)(p,MOVE,x,y);
                if (buf!=buf1)
                    (*p->func) (p.NEWBUF,buf);
                {
                putPtr(p); putInt(x); putInt(y); putPtr(buf);
                break;
        case ERASE:/* erase, de-register, destroy field */
            getPtr(&p); getInt(&x1); getInt(&y1); getPtr(&buf1);
            (*p->func)(p,ERASE);
            de_register_field(p);
            destroy_text_field_object(p);
            break;
}}
```

Although it has nothing to do with differential evaluation per se, the guiding principle in the design of input objects was to avoid needless data redundancy, in the interests of correct display. So, for example, if a data entry field were to provide input for a specific application data variable or buffer, it would do so directly, rather than having to be loaded and unloaded by the application program. Wherever buffering was desired, the application programmer would have to provide it explicitly.

DISCUSSION

Time Efficiency

The time taken to perform an UPDATE invocation, independent of any drawing or erasing time, is proportional to N, where N is the number of data stored in the FIFO, and it is roughly proportional to the number of currently visible display primitives. This is because FIFO operations and comparisons of old and new parameters tend to be the dominant CPU activities. Owing to the small amount of code being executed per object, and the fact that the code is compiled, the constant of proportionality is small enough that images of reasonable complexity can be updated fast enough for most purposes.

As an example, to update a binary tree display generally takes less than 500 machine instructions per visible node, in the absence of any changes. For a tree of 32 nodes, on a 1 MIP computer, update time is under 16 ms. Most modern computers are much faster than 1 MIP and so would perform the update even more quickly.

Space Efficiency

In the simple form of the differential evaluation technique, the FIFO is the only dynamic storage needed for updating the display. The storage consumed is simply the sum of the parameters for all the visible objects and control statements. The data is compact in the FIFO, and there is no overhead for object type information, pointer structures, etc. There is no need for garbage collection or compaction. As an example, in the binary tree display, the storage per node is about 20 bytes (see Diagram 6) or 640 bytes for a 32-node tree. Therefore, the technique is practical even in limited-storage applications.

Robustness

Several years' experience with differential evaluation have taught that it is extremely robust, provided it is understood by the programmer that the sublanguage in which display procedures are written really is a separate language having its own simple rules. These are easily enforced if the implementation of the language has its own parser/preprocessor. Otherwise careful coding suffices. The rules are:

1. Expressions that yield values must never, in general, be computed in ERASE mode. In the implementation in Diagram 5, this is seen as liberal use of the macro X(expr), which protects its argument from being evaluated in ERASE mode. The CALL macro serves the same purpose, where arguments are passed to subroutines. The reason is that ERASE mode exists only for the purpose of deleting objects from the screen and the FIFO. Current data is not merely irrelevant; it may not even exist if, for example, it is pointer-based.

2. Control structure statements must be limited to those provided as part of the language: IF, FOR, CALL, etc. The reason is to guarantee that the FIFO remains synchronized with the state of the display procedure. For example, a Goto statement could cause an END statement to be missed, causing the mode not to be reset. New control structure statements can be created as long as they are careful to keep the FIFO synchronized. For example, it would be handy to have a statement to execute a procedure pointed at by a pointer variable. This would be an implicit conditional, so if the value of the pointer changed, it would be necessary to run the old procedure in ERASE mode and the new one in SHOW mode.

Relation to Object-Oriented Programming

At the time of this writing, object-oriented programming (OOP)[8] is often considered the paradigm of choice for dynamic graphics. A simple view of graphical OOP holds that a display consists of objects. Each object has a data record and a procedure. Things are done to the object by sending messages to its procedure. Since it can trap all activities concerning it, it can in principal maintain any corresponding data, such as its pixel image. For example, an object representing an aircraft could respond to messages to SHOW, ERASE, or MOVE itself, or respond to a clock TICK message by moving itself.

Under differential evaluation, the display procedure view( ) could be considered a tree of objects, one for each graphical primitive and conditional grouping. The messages are SHOW, UPDATE, and ERASE. The memory of the objects is retained in the FIFO, The association between the data and procedure for each object is enforced by the predictable execution sequence, rather than by data structure, as in traditional OOP. In addition, the specific discipline by which these objects control each other is a central aspect of differential evaluation, whereas it is unspecified in general OOP.

Experience

In one application, differential evaluation was made a central part of the user interface support package. The application was a computer integrated manufacturing (CIM) system having some 200 different displays to be shown on about ten terminals of two different types connected to a central VAX computer via 9600-baud RS232 lines.

In another application, it was used as part of a communications network monitoring product, in which the need was for a highly reactive character-graphic display on simple dial-up terminals. The host computer was a 68000-based UNIX machine.

In another application, a prototype of a computer-aided software engineering (CASE) tool, it was used as the main display engine for maintaining multi-window views of complex (200-entity) database designs. The platforms were a Symbolics Lisp Machine and a 386-based PC running Common Lisp.

Another application was part of a Microsoft Windows based program for designing dynamic advertising displays.

The author has developed several small PC-based versions used in a variety of demonstration programs. One of these is a program called DynaDraw, available as shareware on the CompuServe LOGO Forum. Another is an algorithm animation program called ANIMAL available in CompuServe on the Dr. Dobb's Journal (DDJ) Forum.

REFERENCES

1. Roger B. Dannenberg, 'A Structure for efficient update, incremental redisplay and undo in graphical editors', *Software-Practice and Experience*, 20, 109–132 (1990)
2. David Oarlan, 'Views for tools in integrated environments', Ph.D., *Dissertation*. Carnegie Mellon University, May 1987, published as Repo) CMEI-CS-87-147
3. Marc H. Brown, 'Algorithm animation', Ph.D. *Dissertation*, Brown University, April 1987; published as Report CS-87-05
4. Donald E. Knuth, *The Art of Computer Programming*, Volume 1, *Fundamenta/Algorkhm*, Addison Wesley, Reading, Mass., 1973
5. Brian M, Kernighan and Dennis M. Ritchie, *The C Programming Language*, Prentice-Hall, Englewood Cliffs, N.J., 1979
6. Draft Proposal, American National Standard, Graphic Kernel System, Computer *Graphics, Special GKS issue, a quarterly report of ACM SIGGRAPH*, February 1984
7. James D. Foley, Andries van Dam, Steven K. Feiner and John F. Hughes, *Computer Graphics: Principles and Practice*, Addison-Wesley, Reading, Mass., 1990.
8. A. J. Goldberg and D. Robson, Smalltalk-80: *The Language and Its Implementation*, Addison-Wesley, Reading, Mass., 1983

What is claimed is:

1. A computer-implemented method for pharmacological computational model construction, comprising:
    (a) presenting a graphical user interface having a plurality of objects, each object representing one or both of a pharmacokinetic element and a pharmacodynamic element;
    (b) receiving instructions via the graphical user interface for connection of at least two of the objects;
    (c) displaying the at least two objects connected in accordance with the received instructions;
    (d) converting the at least two connected objects into equations corresponding to the pharmacokinetic and pharmacodynamic elements represented by the at least two connected objects, wherein the converting step (d) occurs substantially coincident with the object displaying step (c); and
    (e) displaying the equations on the graphical user interface substantially coincident with the object displaying step (c).

2. The method of claim 1, wherein the converting step (d) comprises:
    (f) converting the at least two connected objects into an internal format; and
    (g) converting the internal format into a surface syntax.

3. The method of claim 2, wherein the surface syntax represents differential equations in an integrator equals rate expression format.

4. The method of claim 2, wherein the objects comprise one of more of compartment blocks, flow blocks, response blocks, and formulation blocks.

5. A computer-implemented method for pharmacological computational model
    (a) presenting a graphical user interface having a plurality of objects, each object representing one or both of a pharmacokinetic element and a pharmacodynamic element;
    (b) receiving instructions via the graphical user interface for connection of at least two of the objects;
    (c) displaying the at least two objects connected in accordance with the received instructions;
    (d) converting the at least two connected objects into an internal format corresponding to the pharmacokinetic and pharmacodynamic elements represented by the at least two connected objects, wherein the converting step (d) occurs substantially coincident with the object displaying step (c);
    (e) interpreting the internal format to generate a time-based simulation including calculation of one or more selected variables;
    (f) plotting the one or more selected variables in a graph; and
    (g) repeating the interpreting and plotting steps (e) and (f), thereby actively updating the graph as the instructions are received in step (b).

6. The method of claim 5, further comprising:
    (h) receiving commands via the graphical user interface to modify at least one of the one or more selected variables; and
    (i) modifying the interpreting step (e) in response to the received commands in step (b); thereby actively updating the graph to reflect changes to the at least one of the one or more selected variables.

7. The method of claim 6, wherein the modifying step (i) comprises revising the internal format.

8. The method of claim 6, wherein one or more of the one or more selected variables depend upon a random variable, wherein the interpreting step (e) generates a value for the random variable upon each repetition, and wherein the plotting step (f) plots the one or more selected variables over plots from previous repetitions, thereby showing variability of the one or more selected variables caused by the random variable within a single graph.

9. The method of claim 6, wherein the internal format comprises a parse tree.

10. The method of claim 6, wherein the one or more selected variables comprise least two selected variables, and wherein the plotting step (f) comprises plotting at least ie selected variable versus another selected variable.

11. The method of claim 6, wherein the plotting step (f) comprises plotting the one or more selected variables versus time.

12. The method of claim 5, further comprising:
(j) translating the internal format into text strings representing equations, the equations corresponding to the respective pharmacokinetic and pharmacodynamic elements represented by the two or more connected objects; and
(k) displaying the text strings substantially coincident with the object displaying step (c).

13. The method of claim 12, wherein the objects comprise one or more of compartment blocks, flow blocks, response blocks, and formulation blocks.

14. A computer readable medium having stored thereon one or more sequences of instructions for causing one or more processors to perform steps for enabling construction a graphical pharmacological computational model, the steps comprising:
(a) presenting a graphical user interface having a plurality of objects, each object representing one or both of a pharmacokinetic element and a pharmacodynamic element;
(b) receiving instructions via the graphical user interface for connection of at least two of the objects;
(c) displaying the at least two objects connected in accordance with the received instructions;
(d) converting the at least two connected objects into equations corresponding to the pharmacokinetic and pharmacodynamic elements represented by the at least two connected objects, wherein the converting step (d) occurs substantially coincident with the object displaying step (c); and
(e) displaying the equations on the graphical user interface substantially coincident with the object displaying step (c).

15. The computer readable medium of claim 14, wherein the converting step (d) comprises:
(f) converting the at least two connected objects into an internal format; and
(g) converting the internal formal into a surface syntax.

16. A computer readable medium having stored thereon one or more sequences of instructions for causing one or more processors to perform steps for enabling construction of a graphical pharmacological computational model, the steps comprising:
(a) presenting a graphical user interface having a plurality of objects, each object representing one or both of a pharmacokinetic element and a pharmacodynamic element;
(b) receiving instructions via the graphical user interface for connection of at least two of the objects;
(c) displaying the at least two objects connected in accordance with the received instructions;
(d) converting the at least two connected objects into an internal format corresponding to the pharmacokinetic and pharmacodynamic elements represented by the at least two connected objects, wherein the converting step (d) occurs substantially coincident with the object displaying step (c);
(e) interpreting the internal format to generate a time-based simulation including calculation of one or more selected variables;
(f) plotting the one or more selected variables in a graph; and
(g) repeating the interpreting and plotting steps (e) and (f), thereby actively updating the graph as the instructions are received in step (b).

17. The computer readable medium of claim 16, wherein the steps further comprise:
(h) receiving commands via the graphical user interface to modify at least one of the one or more selected variables; and
(i) modifying the interpreting step (e) in response to the received commands in step (b); thereby actively updating the graph to reflect changes to the at least one of the one or more selected variables.

18. The computer readable medium of claim 17, wherein one or more of the one or more selected variables depend upon a random variable, wherein the interpreting step (e) generates a value for the random variable upon each repetition, and wherein the plotting step (f) plots the one or more selected variables over plots from previous repetitions, thereby showing variability of the one or more selected variables caused by the random variable within a single graph.

19. The computer readable medium of claim 17, wherein the plotting step (f) comprises plotting the one or more selected variables versus time.

20. The computer readable medium of claim 16, wherein the steps further comprise:
(j) translating the internal format into text strings representing equations, the equations corresponding to the respective pharmacokinetic and pharmacodynamic elements represented by the two or more connected objects; and
(k) displaying the text strings substantially coincident with the object displaying step (c).

21. A system configured to present a graphical user interface having a plurality of objects, each object representing one or both of a pharmacokinetic element and a pharmacodynamic element, the graphical user interface enabling construction of a graphical pharmacological computational model, the system comprising:
(a) a processor;
(b) a data storage area; and
(c) an execution area configured to:
(i) receive instructions regarding connection of at least two of the objects;
(ii) display the connected objects in accordance with the instructions;
(iii) convert the at least two connected objects into an internal format corresponding to the pharmacokinetic and pharmacodynamic elements represented by the at least two connected objects, in parallel with the object display;
(iv) interpret the internal format to generate a time-based simulation including calculation of one or more selected variables;
(v) plot the one or more selected variables in a graph; and
(vi) repeat the interpreting and plotting, thereby actively updating the graph as the instructions are received.

22. The computer system of claim 21, wherein the execution area is further configured to:
(a) receive commands via the graphical user interface to modify at least one of the one or more selected variables; and (b) modify the interpreting in response to the received commands; thereby actively updating the graph to reflect changes to the at least one of the one or more selected variables.

23. The computer system of claim 22, wherein one or more of the one or more selected variables depend upon a random variable, and wherein the plots occur over previous plots, thereby showing variability of the one or more selected variables caused by the random variable within a single graph.

24. The computer system of claim 23, wherein the plots are of the one or more selected variables versus time.

25. The computer system of claim 24, wherein each of the one or more selected variables is plotted using a different color.

26. The computer system of claim 21, wherein the execution area is further configured to:
 (a) translate the internal format into text strings representing equations corresponding to the pharmacokinetic and pharmacodynamic elements represented by the connected objects; and
 (b) display the text strings in parallel with the object display.

* * * * *